US008841108B2

(12) United States Patent
Sagi et al.

(10) Patent No.: US 8,841,108 B2
(45) Date of Patent: Sep. 23, 2014

(54) ANTIBODIES AND PHARMACEUTICAL COMPOSITIONS CONTAINING SAME USEFUL FOR INHIBITING ACTIVITY OF METALLOPROTEINS

(75) Inventors: Irit Sagi, Rehovot (IL); Tamar Danon, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/175,978

(22) Filed: Jul. 5, 2011

(65) Prior Publication Data

US 2012/0003236 A1 Jan. 5, 2012

Related U.S. Application Data

(60) Continuation of application No. 12/382,248, filed on Mar. 11, 2009, now abandoned, which is a division of application No. 10/551,715, filed as application No. PCT/IL2004/000308 on Apr. 4, 2004, now Pat. No. 7,524,938.

(60) Provisional application No. 60/460,005, filed on Apr. 4, 2003.

(51) Int. Cl.
*C12N 9/52* (2006.01)
*C07K 16/00* (2006.01)
*C07K 16/44* (2006.01)
*A61K 39/395* (2006.01)
*C07K 16/40* (2006.01)

(52) U.S. Cl.
CPC .............. *A61K 39/395* (2013.01); *C07K 16/44* (2013.01); *C07K 16/40* (2013.01)
USPC .................. 435/188.5; 530/388.26

(58) Field of Classification Search
CPC ................................ C07K 16/40; C07K 16/44
USPC ......................................................... 435/188.5
See application file for complete search history.

(56) References Cited

U.S. PATENT DOCUMENTS

| 5,672,334 A | 9/1997 | Ranney |
| 2007/0172482 A1 | 7/2007 | Sagi et al. |
| 2009/0208510 A1 | 8/2009 | Sagi et al. |

FOREIGN PATENT DOCUMENTS

| EP | 0757984 | 2/1997 |
| EP | 0780386 | 6/1997 |
| WO | WO 90/05719 | 5/1990 |
| WO | WO 93/20047 | 10/1993 |
| WO | WO 95/09841 | 4/1995 |
| WO | WO 95/29689 | 11/1995 |
| WO | WO 95/29892 | 11/1995 |
| WO | WO 96/06074 | 2/1996 |
| WO | WO 97/24117 | 7/1997 |
| WO | WO 97/49679 | 12/1997 |
| WO | WO 03/044058 | 5/2003 |
| WO | WO 2004/087042 | 10/2004 |

OTHER PUBLICATIONS

Communication Pursuant to Article 94(3) EPC Dated Jun. 3, 2008 From the European Patent Office Re.: Application No. 04725641.7.
Communication Pursuant to Article 94(3) EPC Dated Mar. 30, 2009 From the European Patent Office Re.: Appliction No. 04725641.7.
Communication Pursuant to Rule 58 EPC or Rule 159 EPC, Invitation to Remedy Deficiencies in the Application Document Dated Dec. 2, 2010 From the European Patent Office Re. Application No. 10013205.9.
Communication Pursuant to Rules 70(2) and 70a(2) EPC and Reference to Rule 39(1) EPC Dated Jun. 14, 2011 From the European Patent Office Re. Application No. 10013205.9.
European Search Report and the European Search Opinion Dated May 6, 2011 From the European Patent Office Re. Application No. 10013205.9.
Notice of Allowance Dated Jan. 11, 2011 From the Israel Patent Office Re. Application No. 171156.
Office Action Dated Dec. 7, 2008 From the Israeli Patent Office Re.: Application No. 171156 and Its Translation Into English.
Office Action Dated Oct. 28, 2009 From the Israel Patent Office Re.: Application No. 171156 and Its Translation Into English.
Official Action Dated Aug. 2, 2010 From the US Patent and Trademark Office Re.: U.S. Appl. No. 12/382,248.
Official Action Dated Jan. 3, 2011 From the US Patent and Trademark Office Re.: U.S. Appl. No. 12/382,248.
Official Action Dated Nov. 6, 2009 From the US Patent and Trademark Office Re.: U.S. Appl. No. 12/382,248.
Official Action Dated Mar. 18, 2008 From the US Patent and Trademark Office Re.: U.S. Appl. No. 10/551,715.
Official Action Dated Jan. 19, 2010 From the US Patent and Trademark Office Re.: U.S. Appl. No. 12/382,248.
Summons to Attend Oral Proceedings Pursuant to Rule 115(1) EPC Dated Aug. 13, 2010 From the European Patent Office Re.: Appliction No. 04725641.7.
Supplementary Partial European Search Report Dated Mar. 10, 2008 From the European Patent Office Re.: Application No. 04725641.7.
Almog et al. "Condensation of Tetraaldehydes With Pyrrole. Direct Synthesis of 'Capped' Porphyrins", Journal fo the American Chemical Society, 97(1): 226-227, 1975.
Almog et al. "Synthesis of 'Capped Porphyrins'", Tetrahedron, 37(21): 3589-3601, 1981.
Armstrong et al. "Structural Remodelling in Heart Failure: Gelatinase Induction", Canadian Journal of Cardiology, 10(2): 214-220, 1994.
Axisa et al. "Prospective, Randomized, Double-Blind Trial Investigating the Effect of Doxycycline on Matrix Metalloproteinase Expression Within Atherosclerotic Carotid Plaques", Editorial Comment, Stroke, 33: 2858-2864, 2002.
Baldwin et al. "Synthesis of Iron(II) 'C2-Capped Strapped' + Porphyrin Complexes and Their Reaction With Dioxygen", Journal of the Chemical Society, Dalton Transactions, p. 1739-1746, 1984.
Banerji et al. "A Lymphocite-Specific Cellular Enahncer Is Located Downstream of the Joining Region in Immunoglobulin Heavy Chain Genes", Cell, 33: 729-740, 1983.

(Continued)

*Primary Examiner* — Tekchand Saidha
*Assistant Examiner* — Md. Younus Meah

(57) ABSTRACT

A method of producing a metalloprotein inhibitor, the method comprising generating antibodies directed at a composition including a metal ion-bound chelator, wherein the composition is selected having structural and electronic properties similar to a functional domain of the metalloprotein, thereby producing the metalloprotein inhibitor.

6 Claims, 10 Drawing Sheets

(8 of 10 Drawing Sheet(s) Filed in Color)

(56) References Cited

OTHER PUBLICATIONS

Battersby et al. "Synthetic Studies Related to Myoglobin: Syntheses of Bridged Porphyrin Systems" Journal of the Chemical Society Chemical Communications, p. 879-891, 1976.
Battersby et al. "Sythetic Routes to Singly and Doubly Bridged Porphyrins", Tetrahedron Letters, 34: 3169-3172, 1978.
Belaaouaj et al. "Human Macrophage Metalloelastase. Genomic Organization, Chromosomal Location, Gene Linkage, and Tissue-Specific Expression", The Journal of Biological Chemistry, 270(24): 14568-14575, 1995.
Bird et al. "Single-Chain Antigen-Binding Proteins", Science, 242(4877): 423-426, 1988.
Bode et al. "Endoproteinase-Protein Inhibitor Interactions", APMIS, 107: 3-10, 1999.
Bode et al. "Structural Properties of Matrix Metalloproteinases", CMLS, Cellular and Molecular Life Sciences, 55: 639-652, 1999.
Bode et al. "The X-Ray Crystal Structure of the Catalytic Domain of Human Neutrophil Collagenase by a Substrate Analogue Reveals the Essentials for Catalysis and Specificity", The EMBO Journal, 13(6): 1263-1269, 1994.
Boitrel et al. "Synthesis of 'Gyroscope-Like' Porphyrins", Journal of the Chemical Society, Chemical Communications, p. 1820-1821, 1985.
Borkakoti "Matrix Metalloproteases: Variations on the Theme", Progress in Biophysics & Molecular Biology, 70: 73-94, 1998.
Brown et al. "Potent and Selective Mechanism-Based Inhibition of Gelatinases", Journal of the American Chemical Society, 122: 6799-6800, 2000.
Byrne et al. "Multiplex Gen Regulation: A Two-Tiered Approach to Transgene Regulation in Transgenic Mice", Proc. Natl. Acad. Sci. USA, 86(14): 5473-5477, 1989.
Calame et al. "Transcriptional Controlling Elements in the Immunoglobulin and T Cell Receptor Loci", Advances in Immunology, 43: 235-275, 1988.
Campbell "The Production and Characterization of Rodent and Human Hybridomas", Monoclonal Antibody Technology, Laboratory Techniques in Biochemistry and Molecular Biology, XP002967200, 13: 1-32 (Pocket Ed.), Jan. 1, 1984.
Cawston et al. "A Rapid and Reproducible Assay for Collagenase Using [1-14C]Acetylated Collagen", Analytical Biochemistry, 99: 340-345, 1979.
Cawston et at "Mammalian Collagenases", Methods in Enzymology, 80(Chap.52): 711-722, 1981.
Cawston et al. "Purification of Rabbit Bone Inhibitor of Collagenase", Biochemical Journal, 195: 159-165, 1981.
Cole et al. "Human Monoclonal Antibodies", Molecular and Cellular Biochemistry, 62: 109-120, 1984.
Collman et al. "Effect of Axial Base on Dioxygen and Carbon Monoxide Affinities of Iron(II) Porphyrins. Imidazole Vs. Pyridine", Inorganic Chemistry, 22: 1427-1432, 1983.
Collman et al. "'Picket Fence Porphyrins'. Synthetic Models for Oxygen Binding Hemoproteins", Journal of the American Chemical Society 97(6): 1427-1439, 1975.
Collman et al. "Reversible Oxygen Adduct Formation in Ferrous Complexes Derived From a 'Picket Fence' Porphyrin. A Model for Oxymyoglobin", Journal of the American Chemical Society, 95(23): 7868-7870, 1973.
Cote et al. "Generation of Human Monoclonal Antibodies Reactive With Cellular Antigens", Proc. Natl. Acad. Sci. USA, 80(7)[Part 1: Biological Sciences]: 2026-2030, 1983.
Crowe et al. "A Metalloproteinase Inhibitor Blocks Shedding of the 80-KD TNF Receptor and TNF Processing in T Lymphocytes", Journal of Experimental Medicine, 181: 1205-1210, 1995.
Davidson et al. "The Inhibition of Matrix Metalloproteinase Enzymes", Chemistry and Industry, &: 258-261, 1997.
De Filippis et al. "Structural Studies on the Zinc-Endopeptidase Light Chain of Tetanus Neurotoxin", European Journal of Biochemistry, 229: 61-69, 1995.
De Kruif et al. "Selection and Application of Human Single Chain Fv Antibody Fragments From a Semi-Synthetic Phage Antibody Display Library With Designed CDR3 Regions", Journal of Molecular Biology, 248: 97-105, 1995.
Dean et al. "Evidence for Metalloproteinase and Metalloproteinase Inhibitor Imbalance in Human Osteoarthritic Cartilage", Journal of Clinical Investigation, 84: 678-685, 1989.
Denis et al. "Matrix Metalloproteinase Inhibitors: Present Achievements and Future Prospects", Investigational New Drugs, 15: 175-185, 1997.
Deshpande et al. "A Study of Zinc-Dependent Metalloendopeptidase Inhibitors as Pharmacological Antagonists in Botulinum Neurotoxin Poisoning", Toxicon, 33(4): 551-557, 1995.
Diekmann et al. "Cyclophane Porphyrin", Journal of the American Chemical Society, 93(16): 4068-4070, 1971.
Docherty et al. "The Matrix Metalloproteinases and Their Natural Inhibitors: Prospects for Treating Degenerative Tissue Diseases", Tibtech, 10: 201-207, 1992.
Edlund et al. "Cell-Specific Expression of the Rat Insulin Gene: Evidence for Role of Two Distinct 5$A{\Prime}$ Flanking Elements", Science, 230(4728): 912-916, 1985.
Fingl et al. "Introduction. General Principles", The Pharmacological Basis of Therapeutics, Sec.I(Chap.1): 1-46, 1975.
Fishwild et al. "High-Avidity Human IgGκ Monoclonal Antibodies From a Novel Strain of Minilocus Transgenic Mice", Nature Biotechnology, 14: 845-851, 1996.
Freije et al. "Molecular Cloning and Expression of Collagenase-3, A Novel Human Matrix Metalloproteinase Produced by Breast Carcinomas", The Journal of Biological Chemistry, 269(24): 16766-16773, 1994.
Fridman et al. "Domain Structure of Human 72-Kda Gelatinase/Type IV Collagenase", The Journal of Biological Chemistry, 267(22): 15398-15405, 1992.
Gàlvez et al. "Membrane Type 1-Matrix Metalloproteinase Is Activated During Migration of Human Endothelial Cells and Modulates Endothelial Motility and Matrix Remodeling", The Journal of Biological Chemistry, XP002467839, 276(40): 37491-37500, Oct. 5, 2001. Abstract, p. 37492, 1-h Col.
Gearing et al. "Processing of Tumour Necrosis Factor-α Precursor by Metalloproteinases", Nature, 370: 555-557, 1994.
Gillette et al. "Development and Characterization of Monoclonal Antibodies With Specificity for Metallic Radioisotope Chelators Linked to Antibodies and Other Proteins", Journal of Immunological Methods, XP002467840, 124(2): 277-282, 1989. Abstract, p. 280, r-h Col., Fig.2.
Gogly et al. "Collagen Zymography as a Sensitive and Specific Technique for the Determination of Subpicogram Levels of Interstitial Cellagenase", Analytical Biochemistry, 255: 211-216, 1998.
Gomez et al. "Tissue Inhibitors of Metalloproteinases: Structure, Regulation and Biological Functions", European Journal of Cell Biology, 74: 111-122, 1997.
Gordon et al. "Metalloproteinase Inhibitors as Therapeutics", Clinical and Experimental Rheumatology, 11(Suppl.8): S91-S94, 1993.
Grams et al. "Structure Determination and Analysis of Human Neutrophil Collagenase Complexed With a Hydroxamate Inhibitor", Biochemistry, 34: 14012-14020, 1995.
Hammond et al. "Angiogenic Gene Therapy for Heart Disease: A Review of Animal Studies and Clinical Trials", Cardiovascular Research, 49: 561-567, 2001.
Harada et al. "Control of Photoinduced Electron Transfer From Zinc-Porphyrin to Methyl Viologen by Supramolecular Formation Between Monoclonal Antibody and Zinc-Porphyrin", Photochemistry and Photobiology, 70(3): 298-302, 1999.
Heath et al. "Phase I Trial of the matrix Metalloproteinase Inhibitor BAY 12-9566 in Patients With Advanced Solid Tumors", Cancer Chemotherapy and Pharmacology, 48: 269-274, 20001.
Henriet et al. "Tissue Inhibitors of Metalloproteinases (TIMP) in Invasion and Proliferation", APMIS, 107: 111-119, 1999.
High "Gene Therapy: A 2001 Perspective", Haemophilia, 7(Suppl. 1): 23-27, 2001.
Hill et al "Inhibition of Bone Resorption in Vitro by Selective Inhibitors of Gelatinase and Collagenase", Biochemical Journal, 308: 167-175, 1995.

(56) References Cited

OTHER PUBLICATIONS

Hodgson "Remodeling MMPIs. Matrix Metalloproteinase Inhibitors Will Be Approved as Drugs, Probably This Year, But Questions Remain Concerning Their Specificity, Bioavailability, and Potential Long-Term Toxicity", Bio/Technology, 13: 554-557, 1995.
Huston et al. "Protein Engineering of Antibody Binding Sites: Recovery of Specific Activity in an Anti-Digoxin Single-Chain Fv Analogue Produced in *Escherichia coli*", Proc. Natl. Acad. Sci. USA, 85(16): 5879-5883, 1988.
Inbar et al. "Localization of Antibody-Combining Sites Within the Variable Portions of Heavy and Light Chains", Proc. Natl. acad. Sci. USA, 69(9): 2659-2662, 1972.
Isner "Myocardial Gene Therapy", Nature, 415: 234-239, 2002.
Jones et al. "Replacing the Complementarity-Determining Regions in a Human Antibody With Those From a Mouse", Nature, 321: 522-525, 1986.
Kleifeld et al. "X-Ray Absorption Studies of Human Matrix Metalloproteinase-2 (MMP-2) Bound to a Highly Selective Mechanism-Based Inhibitor. Comparison With the Latent and Active Forms of the Enzyme", The Journal of Biological Chemistry, 276(20): 17125-17131, 2001.
Knight et al. "A Novel Coumarin-Labelled Peptide for Sensitive Continous Assays of the Matrix Metalloproteinases", FEBS Letters, 296(3): 263-266, 1992.
Köhler et al. "Continous Cultures of Fused Cells Secreting Antibody of Predefined Specificity", Nature, 256: 495-497, 1975.
Korkhin et al. "NADP-Dependent Bacterial Alcohol Dehydrogenases: Crystal Structure, Cofactor-Binding and Cofactor Specificity of the ADHs of *Clostridium beijerinckii* and *Thermoanaerobacter brockii*", Journal of Molecular Biology, 278: 967-981, 1998.
Kozbor et al. "Specific Immunoglobulin Production and Enhanced Tumorigenicity Following Ascites Growth of Human Hybridomas", Journal of Immunological Methods, 81: 31-42, 1985.
Larrick et al. "PCR Amplification of Antibody Genes", Methods: A Companion to Methods in Enzymology, 2(2): 106-110, 1991.
Lecas et al. "Condensation D'Acides Amines sur des Meso-Amino-2-Phenyl Porphyrines", Tetrahedron Letters, 26(8): 1019-1022, 1985.
Lonberg et al. "Antigen-Specific Human Antibodies From Mice Comprising Four Distinct Genetic Modifications", Nature, 368: 856-859, 1994.
Lonberg et al. "Human Autobodies From Transgenic Mice", International Reviews of Immunology, 13: 65-93, 1995.
Maret et al. "The PH Variation of Steady-State Kinetic Parameters of Site-Specific Co2+-Reconstituted Liver Alcohol Dehydrogenase", The Journal of Biological Chemistry, 266(31): 20636-20644, 1991.
Marks et al. "By-Passing immunization: Building High Affinity Human Antibodies by Chain Shuffling", Bio/Technology, 10: 779-783, 1992.
McGeehan et al. "Regulation of Tumour Necrosis Factor-α Processing by a Metalloproteinase Inhibitor", Nature, 370: 558-561, 1994.
Mohler et al. "Protection Against a Lethal Dose of Endotoxin by an Inhibitor of Tumour Necrosis Factor Processing", Nature, 370: 218-220, 1994.
Momenteau et al. "'Basket Handle' Porphyrins and Their Ferrous Complexes as Stable Oxygen Carriers", Nouveau Journal de Chimie, 3(2): 77-79, 1979.
Momenteau et al. "'Basket Handle' Porphyrins: New Synthetic Iron (II) Complexes for Oxygen Binding", Journal of Molecualr Catalysis, 7: 315-320, 1980.
Momenteau et al. "Both-Faces Hindered Porphyrins. Part 1. Synthesis and Characterization of Basket-Handle Porphyrins and Their Iron Complexes", Journal of Chemical Society Perkin Transactions, 1: 189-196, 1983.
Morgunova et al. "Structure of Human Pro-Matrix Metalloproteinase-2: Activation Mechanism Revealed", Science, 284(5420): 1667-1670, 1999.

Morrison "Success in Specification", Nature, 368: 812-813, 1994.
Nagase et al. "Matrix Metalloproteinases", The Journal of Biological Chemistry, XP002191132, 274(31): 21491-21494, Jul. 30, 1999. p. 21491, 1-h Col., Last §, Figs.1, 2.
Nakada et al. "Expression and Tissue Localization of Membrane-Type 1, 2, and 3 Matrix Metalloproteinases in Human Astrocytic Tumors", American Journal of Pathology, 154(2): 417-428, 1999.
Netzel-Arnett et al. "Continuously Recording Fluorescent Assays Optimized for Five Human Matrix Metalloproteinases", Analytical Biochemistry, 195: 86-92, 1991.
Neuberger "Generating High-Avidity Human Mabs in Mice", Nature Biotechnology, 14: 826, 1996.
Newby et al. "Extracellular Matrix Degrading Metalloproteinases in the Pathogenesis of Arteriosclerosis", Basic Research in Cardiology, 89(Suppl.1): 59-70, 1994.
O'Connor et al. "Matrix Metalloproteinases and Lung Disease", Thorax, 49: 602-609, 1994.
Orlandi et al. "Cloning immunoglobulin Variable Domains for Expression by the Polymerase Chain Reaction", Proc. Natl. Acad. Sci. USA, 86(10): 3833-3837, 1989.
Pack et al. "Improved Bivalent Miniantibodies, With Identical Avidity as Whole Antibodies, Produced by High Cell Density Fermentation of *Escherichia coli*", Bio/Technology, 11: 1271-1277, 1993.
Payne "Metallo-β-Lactamases—A New Therapeutic Challenge", Journal of Medical Microbiology, 39: 93-99, 1993.
Pinkert et al. "An Albumin Enhancer Located 10 Kb Upstream Functions Along With Its Promoter to Direct Efficient, Liver-Specific Expression in Transgenic Mice", Genes & Development, 1: 268-276, 1987.
Porter "The Hydrolysis of Rabbit γ-Globulin and Antibodies With Crystalline Papain", Biochemical Journal, 73: 119-126, 1992.
Presta "Antibody Engineering", Current Opinion in Structural Biology, 2: 593-596, 1992.
Rasmussen et al. "Matrix Metalloproteinase Inhibition as A Novel Anticancer Strategy: A Review With Special Focus on Batimastat and Marimastat", Pharmacology & Therapy, 75(1): 69-75, 1997.
Ray et al. "The Role of Matrix Metalloproteases and Their Inhibitors in Tumour Invasion, Metastasis and Angiogenesis", European Respiratory Journal, 7: 2062-2072, 1994.
Rehr et al. "Theoretical X-Ray Absorption Fine Structure Standards", Journal of American Chemical Society, 113(14): 5135-5140, 1991.
Reponen et al. "Molecular Cloning of Murine 72-Kda Type IV Collagenase and Its Expression During Mouse Development", The Journal of Biological Chemistry, 267(11): 7856-7862, 1992.
Ricoux et al. "Hemoabzymes: Towards New Biocatalysts for Selective Oxidations", Journal of Immunological Methods, XP004387956, 269(1-2): 39-57, Nov. 2002. Abstract.
Riechmann et al. "Reshaping Human Antibodies for Therapy", Nature, 332: 323-327, 1988.
Ross et al. "Chelometric Indicator Titrations With the Solid-State Cupric Ion-Selective Electrode", Analytical Chemistry, 41(13): 1900-1902, 1969.
Sato et al. "A Matrix Metalloproteinase Expressed on the Surface of Invasive Tumour Cells", Nature, 370: 61-65, 1997.
Schwabacher et al. "Metalloselective Anti-Porphyrin Monoclonal Antibodies", Journal of the American Chemical Society, JACS, 111: 2344-2346, 1989.
Schwartz et al. "Synthetic Inhibitors of Bacterial and Mammalian Interstitial Collagenases", Progress in Medicinal Chemistry, 29(Chap.8): 271-334, 1992.
Shapiro et al. "Cloning and Characterization of a Unique Elastolytic Metalloproteinase Produced by Ithman Alveolar Macrophages", The Journal of Biological Chemistry, 268(32): 23824-23829, 1993.
Singh et al. "Relationship Between Structure and Bioavailability in a Series of Hydroxamate Based Metalloprotease Inhibitors", Bioorganic & Medicinal Chemistry Letters, 5(4): 337-342, 1995.
Somia et al. "Gene Therapy: Trials and Tribulations", Nature Reviews/Genetics, 1: 91-99, 2000.
Stern et al. "The UWXAFS Analysis Package: Philosophy and Details", Physica B, 208 & 209: 117-120, 1995.
Tonkinson et al. "Antisense Oligodeoxynucleotides as Clinical Therapeutic Agents", Cancer Investigation, 14(1): 54-65, 1996.

(56) References Cited

OTHER PUBLICATIONS

Traylor et al. "Anthracene Heme Cyclophanes. Steric Effects in CO, O2, and RNC Binding", Journal of the American Chemical Society, 107: 604-614, 1985.

Uemori et al. "O2 and CO Binding to 'Jellyfish' Type Iron(II) Porphyrins", Inorganic Chemistry, 28: 1690-1694, 1989.

Van Wart et al. "The Cysteine Switch: A Principle of Regulation of Metalloproteinase Activity With Potential Applicability to the Entire Matrix Metalloproteinase Gene Family", Proc. Natl. Acad. Sci. USA, 87(14): 5578-5582, 1990.

Verhoeyen et al. "Reshaping Human Antibodies: Grafting an Antilysozyme Activity", Science, 239(4847): 1534-1536, 1988.

Walakovits et al. "Detection of Stromelysin and Collagenase in Synovial Fluid From Patients With Rheumatoid Arthritis and Post-traumatic Knee Injury", Arthritis and Rheumatism, 35(1): 35-42, 1992.

Weingarten et al. "Cleavage Site Specificity of Vertebrate Collagenases", Biochemical and Biophysical Research Communications, 139(3): 1184-1187, 1986.

Whitlow et al. "Single-Chain Fv Proteins and Their Fusion Proteins", Methods: A Companion to Methods in Enzymology, 2(2): 97-105, 1991.

Will et al. "The Soluble Catalytic Domain of Membrane Type 1 Matrix Metalloproteinase Cleaves the Propeptide of Progelatinase A and Initiates Autoproteolytic Activation", The Journal of Biological Chemistry, 271(29): 17119-17123, 1996.

Winoto et al. "A Novel, Inducible and T Cell-Specific Enhancer Located at the 3' End of the T Cell Receptor α Locus", The EMBO Journal, 8(3): 729-733, 1989.

Winter et al. "Man-Made Antibodies", Nature, 349: 293-299, 1991.

Zabinsky et al. "Multiple-Scattering Calculations of X-Ray-Absorption Spectra", Physical Review B, 52(4): 2995-3009, 1995.

Zucker et al. "Critical Appraisal of the Use of Matrix Metalloproteinase Inhibitors in Cancer Treatment", Oncogene, 19: 6642-6650, 2000.

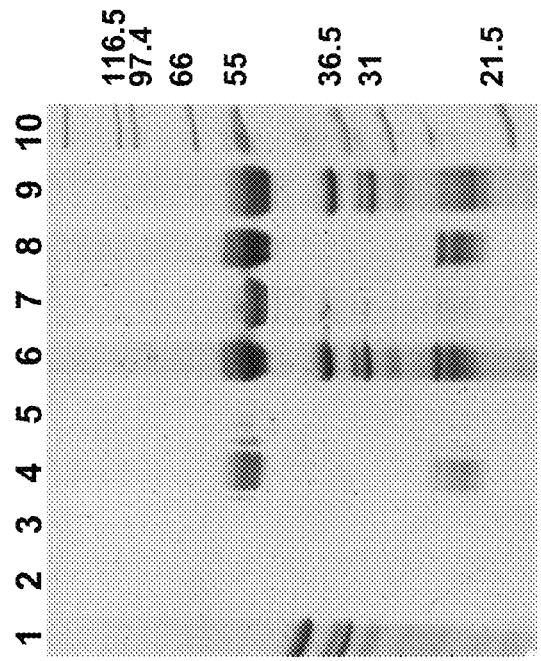
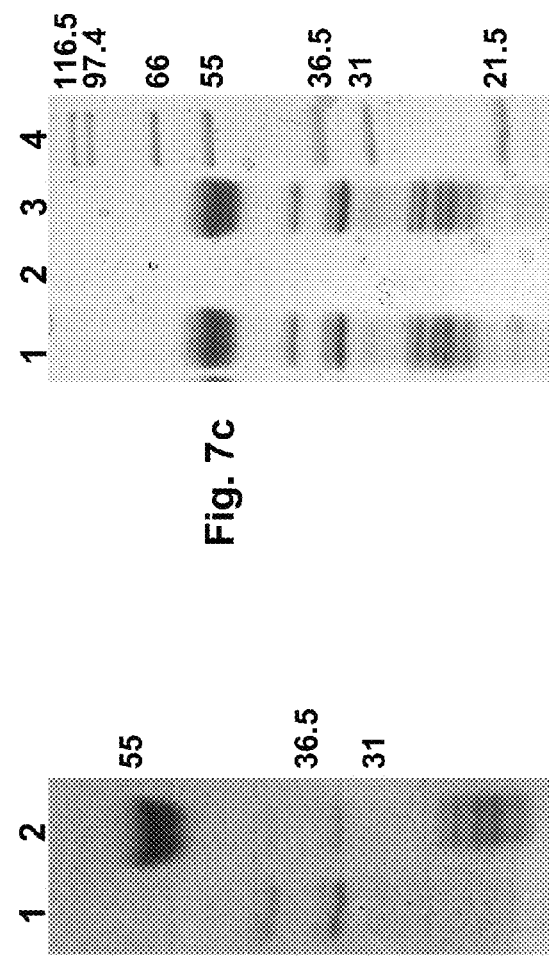
Fig. 7a
Fig. 7b
Fig. 7c

Figs. 11a-b
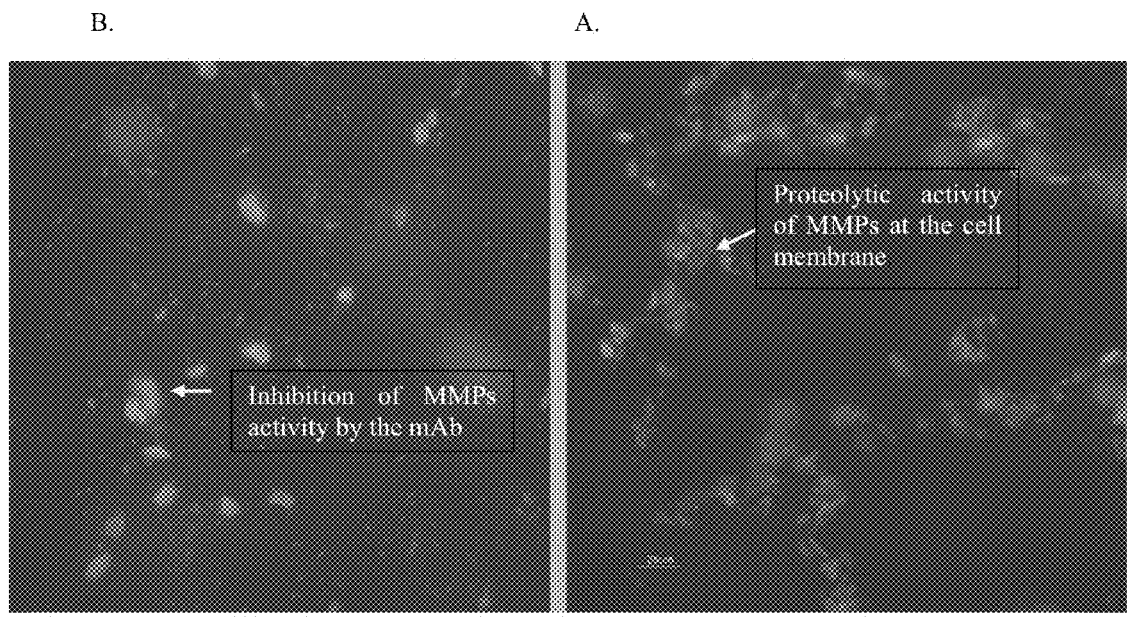

US 8,841,108 B2

ANTIBODIES AND PHARMACEUTICAL COMPOSITIONS CONTAINING SAME USEFUL FOR INHIBITING ACTIVITY OF METALLOPROTEINS

RELATED APPLICATIONS

This application is a continuation of U.S. patent application Ser. No. 12/382,248 filed on Mar. 11, 2009, now abandoned, which is a divisional of U.S. patent application Ser. No. 10/551,715 filed on Jul. 20, 2006, now U.S. Pat. No. 7,524,938, which is a National Phase of PCT Patent Application No. PCT/IL2004/000308 filed on Apr. 4, 2004, which claims the benefit of priority of U.S. Provisional Patent Application No. 60/460,005, filed on Apr. 4, 2003. The contents of the above Applications are all incorporated herein by reference.

FIELD AND BACKGROUND OF THE INVENTION

The present invention relates to antibodies and fragments thereof which can be used to inhibit activity of metalloproteins, such as metalloproteases, and to methods which utilize same for treating diseases such as metastatic cancer which are associated with abnormal activity of a metalloprotein.

The matrix metalloproteins (MMPs) are key enzymes participating in remodeling of the extracellular matrix (ECM). These enzymes are capable of destroying a variety of connective tissue components of articular cartilage or basement membranes.

The human MMP gene family consists of at least 28 structurally related proteins (see FIG. 1), which share a similar overall spherical topology (FIG. 2 and Borkakoti, 1998). Each MMP is secreted as an inactive, latent pro-enzyme. The catalytic zinc domain is composed of about 180 amino acids wherein the highly conserved sequence HE-GH-LGL-H provides the three histidine (i.e., H) residues which bind to the metal Zn(2+) ion. The forth-binding site of the catalytic zinc ion in the pro-enzyme is bound to a cystein residue (Morgunova et al., 1999), which upon enzyme activation dissociates from the active site (Van Wart and Birkedal-Hansen, 1990). As a result, the forth-binding site in the activated MMPs is taken up by a water molecule, which is also hydrogen-bonded to a conserved glutamic residue. This process facilitates the hydrolysis of a peptide bond of the target substrate with the activated water molecule.

The uncontrolled breakdown of connective tissue by metalloproteases is a feature of many pathological conditions, probably resulting from an excess of MMP activity or from an imbalanced ratio between the natural MMP tissue inhibitors (TIMPs) and MMPs. TIMPs inhibit MMPs by forming stoichiometric complexes with the active zinc binding site of MMPs (Gomez et al., 1997; Henriet at al., 1999; Bode et al., 1999; Will et al., 1996). When TIMPs levels are insufficient, a progressive slow degradation of the ECM may lead to loss of cartilage matrix in rheumatoid arthritis (Walakovits et al., Arthritis Rheum, 35:35-42, 1992) and osteoarthritis (Dean et al., J. Clin. Invest. 84:678-685, 1989) or bone matrix degradation in osteoporosis (Hill et al., Biochem. J. 308: 167-175, 1995). In other situations, such as congestive heart failure, rapid degradation of the heart's ECM may occur (Armstrong et al., Canadian J. Cardiol. 10: 214-220, 1994).

Other pathological condition, which are also related to unregulated activity of MMPs, include the rapid remodeling of the ECM by metastatic tumor cells. In such conditions the activated MMPs are either expressed by the cancer cells or by the surrounding tissues. There is considerable evidence that MMPs are involved in the growth and spread of tumors (e.g., see Davidson et al., Chemistry & Industry, 258-261, 1997, and references therein). In the process of tumor metastasis, MMPs are used to break down the ECM, allowing primary tumor cancer cells to invade neighboring blood vessels where they are transported to different organs and establish secondary tumors. The invasive growth at these secondary sites is mediated by MMPs, which break down the tissue. In addition, MMP activity contributes to the invasive in-growth of new blood vessels, also termed angiogenesis, which is required for tumors to grow above a certain size.

Given the broad role of MMPs in human physiology and pathology, it is not surprising that numerous efforts have been affected to design drugs, which inhibit MMP excessive activity.

Drug discovery efforts have focused on inhibitor classes that contain a functional group which coordinates the zinc ion to thereby inactivate the target MMP. One such inhibitor class is the hydroxamate inhibitors, small peptide analogs of fibrillar collagens, which specifically interact in a bidentate manner via the hydroxyl and carbonyl oxygens of the hydroxamic group with the zinc ion in the catalytic site [Grams et al., (1995), Biochem. 34: 14012-14020; Bode et al., (1994), EMBO J., 13: 1263-1269].

Hydroxamate-based MMP inhibitors are usually composed of either a carbon back-bone (WO 95/29892, WO 97/24117, WO 97/49679 and EP 0780386), a peptidyl backbone (WO 90/05719, WO 93/20047, WO 95/09841 and WO 96/06074) or a peptidomimetic back-bone [Schwartz et al., Progr. Med. Chem., 29: 271-334 (1992); Rasmussen et al., Pharmacol. Ther., 75: 69-75 (1997); Denis et al., Invest. New Drugs, 15: 175-185 (1997)]. Alternatively, they contain a sulfonamido sulfonyl group which is bonded on one side to a phenyl ring and a sulfonamido nitrogen which is bonded to an hydroxamate group via a chain of one to four carbon atoms (EP 0757984 A1).

Other peptide-based MMP inhibitors are thiol amides which exhibit collagenase inhibition activity (U.S. Pat. No. 4,595,700), N-carboxyalkyl derivatives containing a biphenylethylglycine which inhibit MMP-3, MMP-2 and collagenase (Durette, et al., WO-9529689), lactam derivatives which inhibit MMPs, TNF-alpha and aggrecanase (see U.S. Pat. No. 6,495,699) and Tricyclic sulfonamide compounds (see U.S. Pat. No. 6,492,422).

Although peptide-based MMP inhibitors have a clear therapeutic potential their use in clinical therapy is limited. Peptide-based hydroxamate are costly to produce and have low metabolic stability and oral bioavailability [e.g., batimastat (BB-94)]. These compounds are rapidly glucuronidated, oxidized to carboxylic acid and excreted in the bile [Singh et al., Bioorg. Med. Chem. Lett. 5: 337-342, 1995; Hodgson, "Remodelling MMPIs", Biotechnology 13: 554-557, 1995)]. In addition, peptide-based MMP inhibitors often exhibit the same or similar inhibitory effects against each of the MMP enzymes. For example, batimastat is reported to exhibit $IC_{50}$ values of about 1 to about 20 nM against each of MMP-1, MMP-2, MMP-3, MMP-7, and MMP-9 [Rasmussen et al., Pharmacol. Ther., 75(1): 69-75 (1997)]. Furthermore, the use of several hydroxamate inhibitors was associated with severe side effects such as muscoloskeletal problems with marimastat (BB-2516), widespread maculopapular rash with CGS27023A (Novartis) [Levitt et al., 2001, Clin. Cancer Res. 7: 1912-1922] and liver abnormalities, anemia, shoulder and back pain, thrombocytopenia, nausea, fatigue, diarrhea and deep vein thrombosis with BAY12-9566 (Bayer) [Heath et al., 2001, Cancer Chemother. Pharmacol. 48: 269-274].

Moreover, phase III clinical trials on advanced cancer patients with marimastat, prinomastat (AG 3340, Agouron) and Bay 12-9566 demonstrated no clinical efficacy in inhibiting metastasis (Zucker et al., 2000, Oncogene 19: 6642-50).

Other MMP inhibitors are the chemically modified nonmicrobial tetracyclines (CMTs) that were shown to block expression of several MMPs in vitro. However, in vivo efficacy of these compounds was found to be limited, e.g., the CMT inhibitor, doxycycline, reduced tissue levels of MMP-1 but not MMP-2, 3, or –9 in atherosclerotic carotid plaques in human patients (Axisa et al., 2002, Stroke 33: 2858-2864).

Recently, a mechanism-based MMP inhibitor, SB-3CT, was designed according to the X-ray crystallographic information of the MMP active site (Brown et al., 2000). X-ray absorption studies revealed that binding of this molecule to the catalytic zinc reconstructs the conformational environment around the active site metal ion back to that of the pro-enzyme [Kleifeld et al., 2001, J. Biol. Chem. 276: 17125-31]. However, the therapeutic efficacy obtained with this agent is yet to be determined.

Another class of natural inhibitors is monoclonal antibodies. Several antibodies have been raised against specific peptide sequences within the catalytic domain MMP-1 (Galvez et al., 2001, J. Biol. Chem., 276: 37491-37500). However, although these antibodies could inhibit the in-vitro activity of MMP, results demonstrating the in-vivo effectiveness of such antibodies have not been demonstrated.

As described hereinabove, the catalytic site of MMPs includes a coordinated metal ion which becomes available for substrate binding following enzyme activation (see FIGS. 2a-c). It is thus conceivable that conventional antibodies directed at the primary amino acid sequence of the enzyme would not distinguish the active form from the inactive form of the enzyme and hence would not serve as potent inhibitors of such enzymes.

While reducing the present invention to practice, the present inventors have uncovered that in sharp contrast to the above, antibodies which recognize electronic and structural determinants of the catalytic site of MMPs are potent inhibitors thereof and as such can be used to treat diseases associated with imbalanced MMP activity.

SUMMARY OF THE INVENTION

According to one aspect of the present invention there is provided an antibody or an antibody fragment, comprising an antigen recognition region capable of binding a metal ion and a chelator thereof, wherein the antibody or the antibody fragment is capable of inhibiting an activity of a metalloprotein.

According to another aspect of the present invention there is provided a method of producing a metalloprotein inhibitor, the method comprising generating antibodies directed at a composition including a metal ion-bound chelator, wherein the composition is selected having structural and electronic properties similar to a functional domain of the metalloprotein, thereby producing the metalloprotein inhibitor.

According to yet another aspect of the present invention there is provided an antibody or an antibody fragment, comprising an antigen recognition region capable of binding a metal ion and a chelator thereof, wherein the antibody or the antibody fragment is capable of inhibiting an activity of a matrix metalloprotease.

According to still another aspect of the present invention there is provided a pharmaceutical composition comprising an antibody or an antibody fragment including an antigen recognition region capable of binding a metal ion and a chelator thereof and a physiologically acceptable carrier, wherein the antibody or antibody fragment is capable of inhibiting an activity of a matrix metalloprotease.

According to an additional aspect of the present invention there is provided a matrix metalloprotease inhibitor comprising an antibody or an antibody fragment including an antigen recognition region capable of binding a metal ion and a chelator thereof.

According to yet an additional aspect of the present invention there is provided a method of producing a matrix metalloprotease inhibitor, the method comprising generating antibodies directed at a composition including a metal ion-bound chelator, wherein the composition is selected having structural and electronic properties similar to a catalytic domain of the matrix metalloprotease, thereby producing the matrix metalloprotease inhibitor.

According to still an additional aspect of the present invention there is provided a method of inhibiting matrix metalloprotease activity in a subject in need thereof, the method comprising providing to the subject a therapeutically effective amount of an antibody or an antibody fragment including an antigen recognition region capable of binding a metal ion and a chelator thereof, thereby inhibiting matrix metalloprotease activity in the subject.

According to a further aspect of the present invention there is provided an article-of-manufacture comprising packaging material and a pharmaceutical composition identified for treating diseases associated with abnormal activity of a matrix metalloprotease being contained within the packaging material, the pharmaceutical composition including, as an active ingredient, an antibody or an antibody fragment including an antigen recognition region capable of binding a metal ion and a chelator thereof, wherein the antibody or antibody fragment is capable of inhibiting an activity of the matrix metalloprotease.

According to further features in preferred embodiments of the invention described below, the metal ion is a transition metal ion selected from the group consisting of Vanadium, Selenium, Molybdenum, Cobalt, Zinc, Copper, Iron, Gallium, Bismuth, Aluminum, Gold, Platinum, Manganese, Chronium, Silver, Antimony, Thalium, Cadmium, Nickel, Mercury and Lead.

According to still further features in the described preferred embodiments the chelator is a polyamine.

According to still further features in the described preferred embodiments the polyamine is at least two histidine molecules.

According to still further features in the described preferred embodiments the polyamine is selected from the group consisting of ethylene diamine, cyclam, porphyrin, diethylenetriamine, triethylenetetramine, triethylenediamine, tetraethylenepentamine, aminoethylethanolamine, aminoethylpiperazine, pentaethylenehexamine, captopril, penicilamine, N,N'-bis(3-aminopropyl)-1,3-propanediamine, N,N'-Bis-(2-animoethyl)-1,3-propanediamine, 1,7-dioxa-4,10-diazacyclododecane, 1,4,8,11-tetraaza cyclotetradecane-5,7-dione, 1,4,7-triazacyclononane, 1-oxa-4,7,10-triazacyclododecane, 1,4,8,12-tetraazacyclopentadecane, and 1,4,7,10-tetraazacyclododecane.

According to still further features in the described preferred embodiments the metalloprotein is selected from the group consisting of neutrophil collagenase, collagenase-3, gelatinase A, gelatinase B, stromelysins-2 and 3, matrilysin, macrophage elastase; membrane-type MMPs, agrrecanase, tumor necrosis factor converting enzyme, cytokine convertases, adhesion molecule shedding enzymes, endothelin converting enzyme, angiotensin converting enzyme, neutral endopeptidase, FTSH-bacterial metalloprotease, metallo-lactamase (carbapenases), bacterial toxins and ras farnesyl protein transferase and carbonic anhydrase.

According to yet a further aspect of the present invention there is provided a method of qualifying specificity of an antibody to a metal ion and a chelator thereof, the method comprising determining conformational changes in binding of the metal ion to the chelator thereof following binding of the antibody, to thereby qualify the specificity of the antibody to the metal ion and the chelator thereof.

According to still further features in the described preferred embodiments the antibodies are polyclonal antibodies.

According to still further features in the described preferred embodiments the antibodies are monoclonal antibodies.

According to still a further aspect of the present invention there is provided a method of qualifying specificity of an antibody to a metal ion and a chelator thereof, the method comprising determining electronic changes in the metal ion following binding of the antibody, to thereby qualify the specificity of the antibody to the metal ion and the chelator thereof.

The present invention successfully addresses the shortcomings of the presently known configurations by providing metalloprotein antibodies, such as MMP antibodies, which can be used to treat diseases associated with abnormal MMP activity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
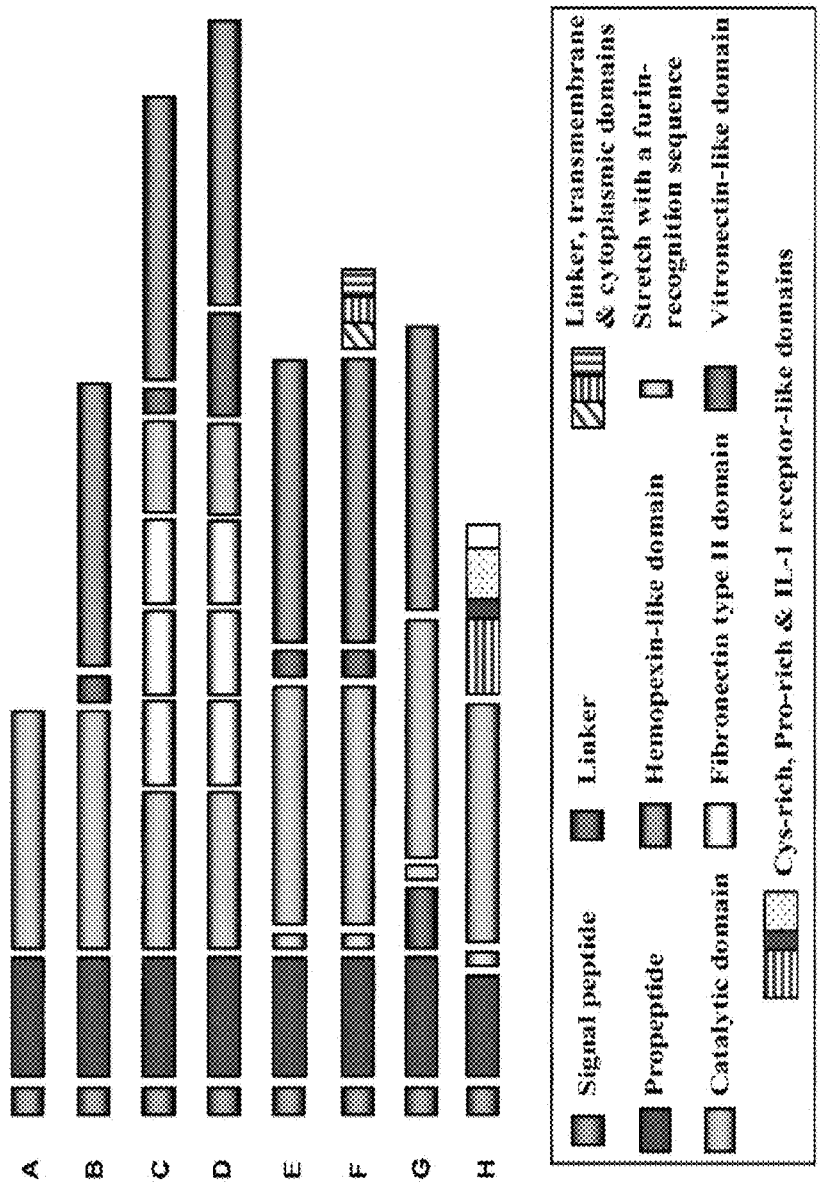

FIG. 1 is a schematic illustration of the MMP protein family domain structure as adapted from Nagase et al., 1999. Shown are the signal peptide, pro-peptide, catalytic, fibronectin type II, linker and hemopexin-like domains. The various groups of domain organization (numbered A through H) represent the structure of the following MMP proteins: A: Matrilysin (MMP-7); B: Collagenase 1 (MMP-1), Stromelysin 1 (MMP-3), Collagenase 2 (MMP-8), Stromelysin 2 (MMP-10), Macrophage elastase (MMP-12), Collagenase 3 (MMP-13), Collagenase 4 (Xenopus, MMP-18), MMP-19, Enamelysin (MMP-20), CMMP (chicken, MMP-22); C: Gelatinase A (MMP-2); D: Gelatinase B (MMP-9); E: Stromelysin 3 (MMP-11); F: MT1-MMP (MMP-14), MT2-MMP (MMP-15), MT3 (MMP-16), MT4 (MMP-17); G: XMMP (Xenopus, MMP-21); and H: MMP-23.

Figure 2B:
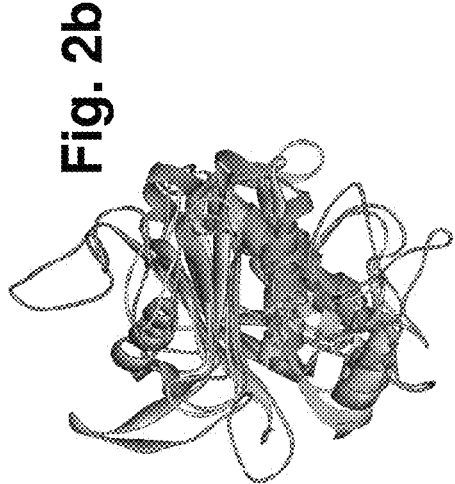
Figure 2C:
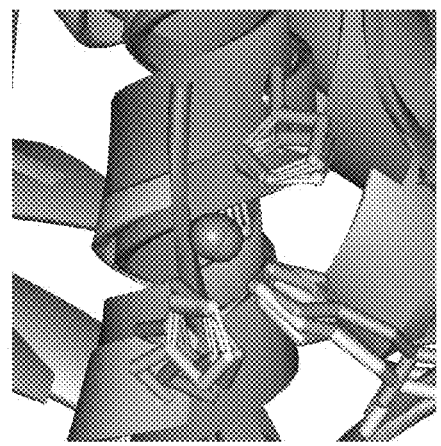
Figure 2A:
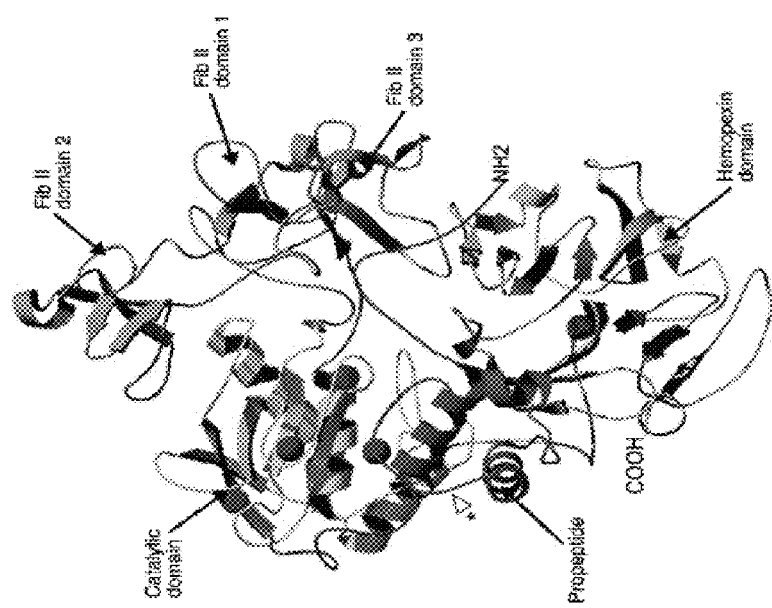

FIG. 2a is a schematic illustration depicting the 3D structure of proMMP-2 as adapted from the protein data bank (PDB): 1CFK (http://www.rcsb.org/pdb) demonstrating the proMMP-2 structural domains: the pro-domain (red), the catalytic domain (blue), the fibronectin type II domains 1-3 (green) and the hemopexin domain (yellow).

FIG. 2b is a schematic illustration of a structural alignment of the catalytic sites in MMP-2, MMP-9, and TACE.

FIG. 2c is a schematic illustration of the structural alignment of FIG. 2b zooming on the metal binding domain.

Figure 3:
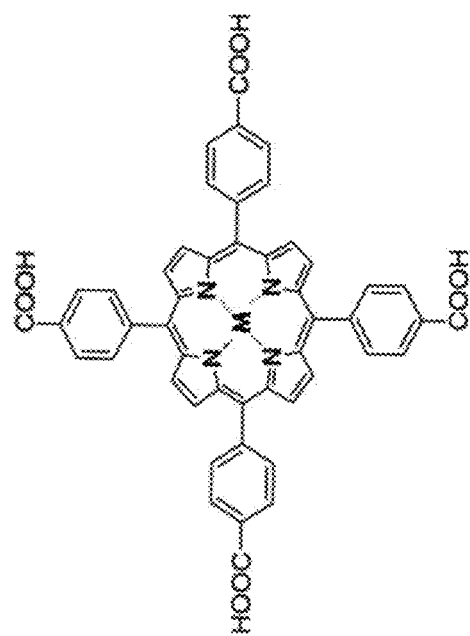

FIG. 3 is a schematic illustration depicting the molecular structure of Co/Zn-TCPP hapten wherein "M" represents Co or Zn.

Figure 4:
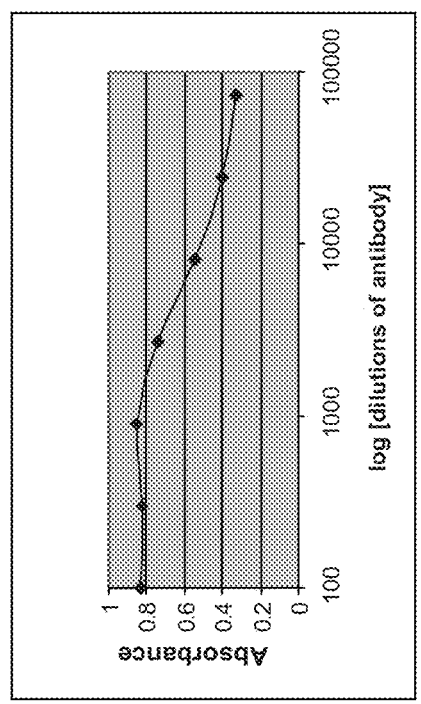

FIG. 4 is a titration curve of the purified Co-TCPP monoclonal antibody. Serial dilutions of the Co-TCPP monoclonal antibody were added to tetra-carboxy phenyl porphyrin Co(II) (Co-TCPP) hapten-coated micro-titer plates. The absorbance of bound antibodies was measured at 280 nm and was plotted against log concentration of the antibody.

Figure 5:
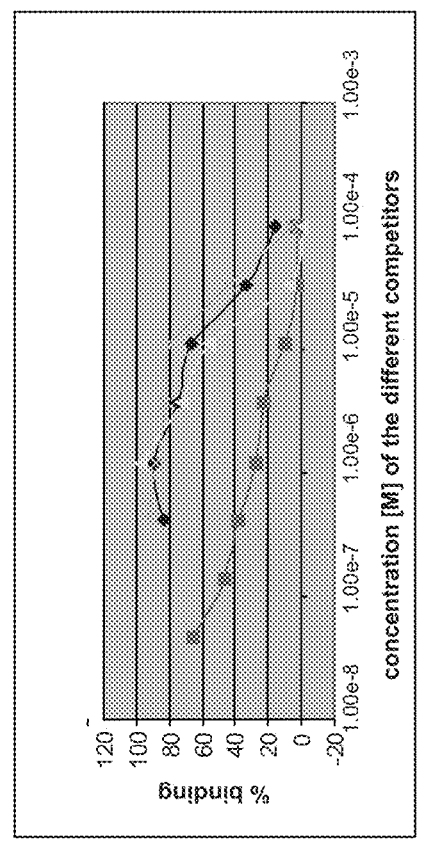

FIG. 5 is a graphic illustration depicting a competitive inhibition assay of the purified Co-TCPP monoclonal antibody binding to the indicated haptens. The antibody was incubated (at $IC_{50}$) with Co-TCPP (purple), TCPP (blue), Zn-TCPP (yellow), Zn-TPP (light blue) haptens at the indicated concentrations and the relative fraction of bound antibodies (% binding) was calculated.

Figure 6A:
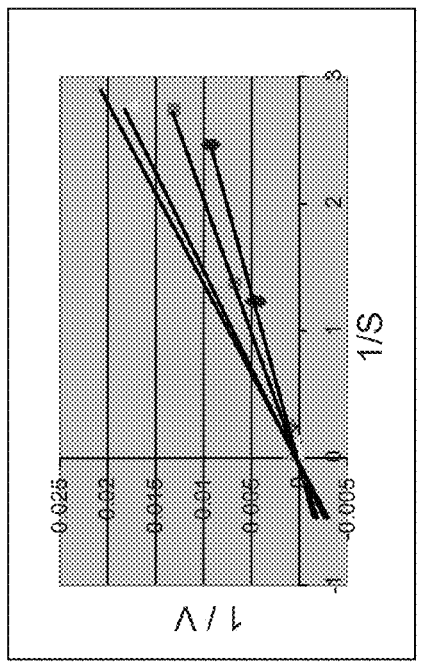
Figure 6B:
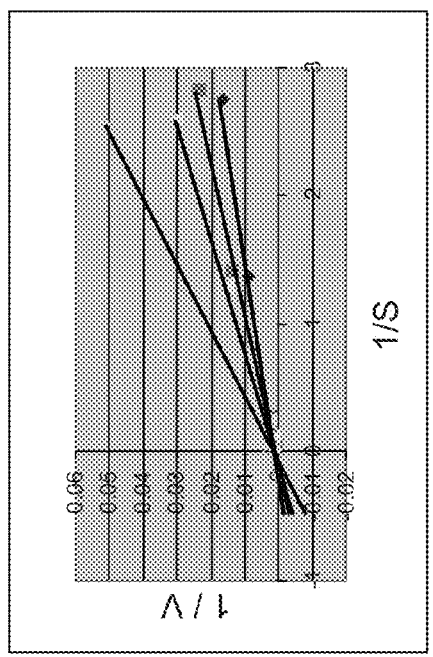

FIGS. 6a-b are Lineweaver-Burk plots of MMP-2 and MMP-9 depicting the hydrolysis of a fluorogenic substrate in the presence of the Co-TCPP monoclonal antibody. The MMP-2 catalytic domain (FIG. 6a) and the MMP-9 full length (FIG. 6b) proteins were incubated with increasing concentrations of the Mca-Pro-Leu-Gly-Leu-Dpa-Ala-Arg-$NH_2$ fluorogenic substrate in the presence of 6 µM (FIGS. 6a-b, purple squares), 18 µM (FIGS. 6a-b, yellow triangles) 24 µM (FIGS. 6a-b, light blue Xs), or absence (FIGS. 6a-b, blue diamonds) of the antibody.

FIG. 7a illustrates an immunoprecipitation (IP) assay of MMP-2 with the Co-TCPP monoclonal antibody. An SDS-PAGE gel loaded with the soluble or pellet phases obtained from the following IP experiments is shown; Incubation of MMP-2 with protein A beads (FIG. 7a, Lane 1: soluble, Lane 2: pellet); incubation of the antibody with protein A beads (Lane 3: soluble, Lane 4: pellet); incubation of MMP-2 with pre-associated antibody-protein A beads (Lane 5: soluble, Lane 6: pellet); incubation of Dead Box Proten A (DbpA) with pre-associated antibody-protein A beads (Lane 7: soluble, Lane 8: pellet) and incubation of MMP-2 with antibody (Lane 9: soluble). Molecular weight marker (1 µg) is shown in Lane 10. Bands were visualized using Coomassie Blue staining.

FIG. 7b illustrates an immunoprecipitation assay of a zinc-free MMP-2. Shown is an SDS-PAGE of the soluble (Lane 1) or pellet (Lane 2) phases obtained by incubating the zinc-free MMP-2 with pre-associated antibody-protein A beads. Bands were visualized using Coomassie blue staining.

FIG. 7c illustrates an immunoprecipitation assay of MMP-2 in the presence or absence of the GM-6001 MMP inhibitor. Shown is an SDS-PAGE of the pellet or soluble phases obtained by the incubation of MMP-2 with pre-associated antibody-protein A beads (pellet phase: Lane 1), or by the incubation of MMP-2 with pre-associated antibody-protein A beads in the presence of GM-6001 (soluble phase: Lane 2, pellet phase: Lane 3). Molecular weight marker (1 μg) is shown in Lane 4. Bands were visualized using Coomassie Blue staining.

Figure 8A:
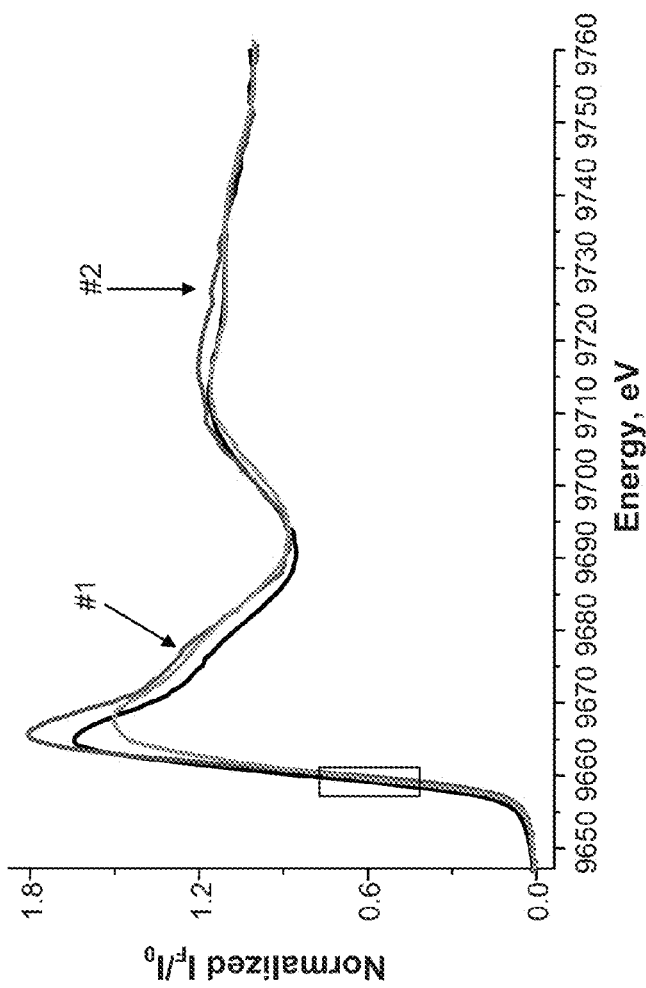
Figure 8B:
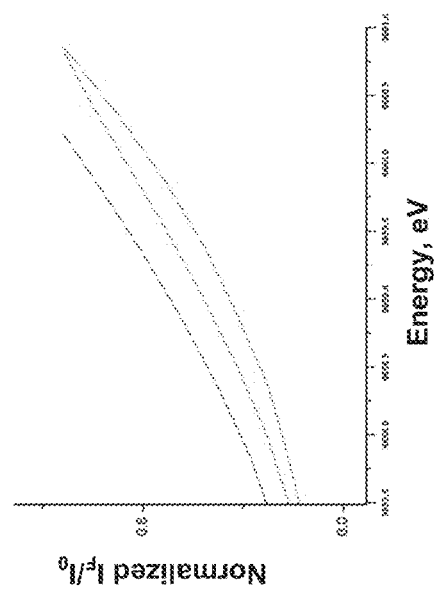

FIGS. 8a-b illustrate the Zinc K-edge spectra of MMP-2. Shown are the normalized X-ray absorption spectroscopy (XAS) data of the full-length latent (FIGS. 8a-b, green), active (FIGS. 8a-b, black) and inhibited (FIGS. 8a-b, red) forms of MMP-2. Note the small peak at 9680 eV (FIG. 8a, arrow 1) and the absence of cleft at 9730 eV (FIG. 8a, arrow 2) in the inhibited enzyme. Also note the distinct shift of 0.86 electron volts (eV) to higher energy between the active and inhibited enzymes (FIG. 8b).

Figure 9:
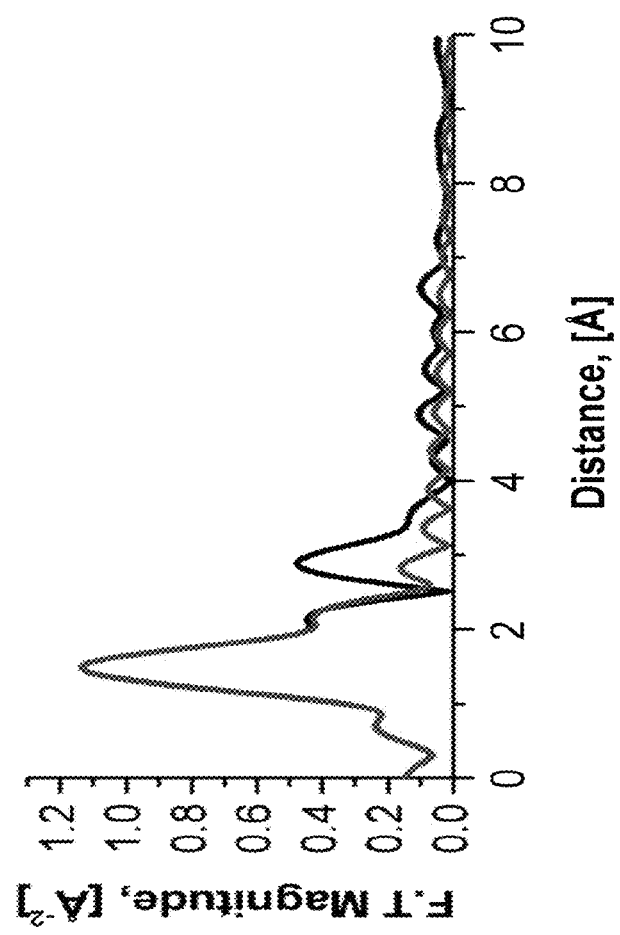

FIG. 9 illustrates an extended X-ray absorption fine structure (EXAFS) analysis of the monoclonal antibody-Zinc immunocomplex. Results are presented in the R-space of the experimental data (black) to simulated theoretical zinc ligand contributions (red).

Figure 10:
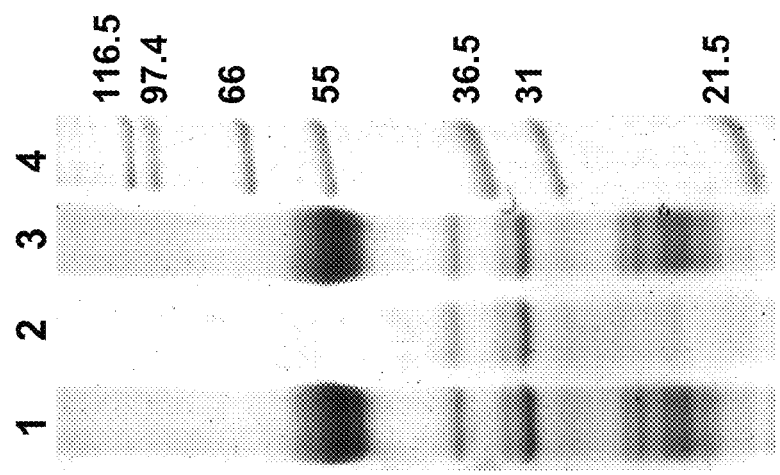

FIG. 10 is an SDS PAGE analysis demonstrating 4-aminophenylmercuric acetate (APMA) binding to MMP-2 immunocomplexes. Recombinant MMP-2 catalytic domain was incubated with pre-associated antibody-protein A beads in the presence or absence of the MMP activator, APMA. Shown is an SDS-PAGE of the soluble or pellet phases obtained following the incubation of MMP-2 with pre-associated antibody-protein A beads (Lane 1, pellet phase) or incubation of MMP-2 with pre-associated antibody-protein A beads in the presence of APMA (FIG. 10, lane 2: soluble, lane 3: pellet). Bands were visualized with Coomassie blue staining.

FIGS. 11a-b are photomicrographs depicting the ability of the mAb of the present invention to block pericellular proteolysis generated by highly invasive fibrocarcoma cancer cells (HT1080), as determined by situ zymography assay. FIG. 11a shows pericellular proteolytic activity of MMP-expres sing HT1080 cells (in light blue; cell nucleui are stained with DAPI). FIG. 11b shows pericellular proteolytic activity of HT1080 cells in the presence of mAb (1 μg). Note, MMP-mediated pericellular proteolysis which appears as green intensity around the cell membrane (FIG. 11a) disappears upon incubation of the cells with the mAb (FIG. 11b).

DESCRIPTION OF THE PREFERRED EMBODIMENTS

The present invention is of antibodies and fragments thereof, which can be used to inhibit metalloprotein activity. Specifically, the antibodies of the present invention can be used to treat diseases associated with imbalanced matrix metalloprotease activity such as metastatic cancers.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Matrix metalloproteases participate in many biological processes, ranging from cell proliferation, differentiation and remodeling of the extracellular matrix (ECM) to vascularization and cell migration. These processes require a delicate balance between the functions of the matrix metalloproteases (MMPs) and natural tissue inhibitors thereof (TIMPs). The loss of this balance is the hallmark of numerous pathological conditions including metastatic tumors, neurodegenerative diseases and osteoarthritis.

Numerous MMP inhibitors are known in the art including small peptide inhibitors such as hydroxomate, non-microbial tetracyclins and monoclonal antibodies. While the former are limited by the high cost of production, high degradability, low oral bioavailability and lack of specificity, none of the latter have demonstrated in-vivo therapeutic efficacy.

While reducing the present invention to practice and while searching for a novel therapeutic modality to clinical conditions associated with imbalanced metalloenzyme activity, the present inventors have uncovered that antibodies which recognize both electronic and structural determinants of the catalytic site of metalloenzymes can be used as potent inhibitors thereof.

These findings enable, for the first time, to generate highly efficient therapeutic antibodies which can be used to treat clinical conditions characterized by elevated metalloprotein activity.

Thus, according to one aspect of the present invention, there is provided a method of producing a metalloprotein inhibitor.

The method is effected by generating antibodies or antibody fragments directed at a composition which includes a metal ion-bound chelator. Such a composition is selected having structural and electronic properties similar to a functional domain, such as a catalytic domain or a substrate binding domain, of the metalloprotein.

As used herein a "metalloprotein" refers to a protein, which includes a bound metal ion as part of a structure thereof. The metal ion may be required for enzymatic activity (i.e., metalloenzyme), either participating directly in catalysis, or stabilizing the active conformation of the protein.

It will be appreciated that all members of the MMP family are translated as latent enzymes, which upon activation are converted into active enzymes in which the metal ion in the active site is accessible for substrate binding. For example, the "cysteine switch model" has been previously suggested to explain MMP in vitro activation. The cysteine switch model suggests that upon activation, the latent zinc-binding site is converted to a catalytic zinc-binding site by dissociation of the thiol (Cys)-bearing propeptide from the zinc atom. Cleavage of the propeptide results in a breakdown of the pro-domain structure of the enzyme, and the shielding of the catalytic zinc ion is withdrawn. Consequently, the metal ion and the active site pocket are accessible for substrate binding and hydrolysis [Van Wart and Birkedal-Hansen (1990) Proc. Natl. Acad. Sci. USA 87, 5578-5582].

Unlike prior art antibodies, the antibodies and antibody fragments of this aspect of the present invention serve as potent inhibitors of MMPs, due to their ability to bind both the metal ion and the coordinating amino acids within the catalytic zinc site, thereby specifically inhibiting the active conformation of these enzymes which are directly involved in pathological processes as described above.

Examples of metalloenzymes which may be inhibited using the teachings of the present invention, include but are not limited to, neutrophil collagenase, collagenase-3, gelatinase A, gelatinase B, stromelysins-2 and 3, matrilysin, macrophage elastase; membrane-type MMPs, agrrecanase, cytokine convertases, adhesion molecule "shedding enzymes", endothelin converting enzyme, angiotensin converting enzyme, neutral endopeptidase, FTSH-bacterial metalloprotease, metallo-lactamase (carbapenases), bacterial toxins e.g., tetanus or botulinum toxins, ras farnesyl protein transferase, carbonic anhydrase and the like. Other examples of metalloenzymes are disclosed in Hodgson, Bio/Technology, 13:554 (1995); Gordon, et al., Clin. Exper. Rheum., 11 (8):S91-S94 (1993); Ray, et al., Eur. Respir. J., 7:2062-2072 (1994); O'Connor, et al., Thorax, 49: 602-609 (1994); Docherty, et al., Tibtech, Vol. 10, (1992); Newby, et al., Basic Res. Cardiol., 89(Suppl):59-70; Freije, et al., J. Biol. Chem., 269(24):16766-16773 (1994); Shapiro, et al., J. Biol. Chem., 268(32):23824-23829 (1993); Belaauoaj, et al., J. Biol. Chem., 27(24):14568-14575 (1995); Gearing, et al., Letters to Nature, Nature, 370:555-557 (1994); McGeehan, et al., Letters to Nature, Nature, 370:558-561 (1994); Mohler, et al., Letters to Nature, Nature, 370:218-220 (1994); Sato, et al., Letters to Nature, Nature, 370:61-65 (1994); Crowe, et al., J. Exp. Med., 181:1205-1210 (1995); Payne, J. Med. Microbiol., 32:93-99 (1993); Deshpande, et al., Toxicon, 33(4): 551-557 (1995); DePhillips, et al., Eur. J. Biochem., 229:61-69 (1995).

As described hereinabove any composition including a metal ion bound to a chelator thereof can be used to generate the antibodies of the present invention, as long as it has structural and electronic (i.e., charge, e.g., charge distribution and/or density) properties similar to that of a functional domain of the metalloprotease. Although use of the actual metal ion-bound chelator domain of the metalloprotein in generating antibodies is preferred, it will be appreciated that in cases wherein such a domain is well characterized, one may synthesize and utilize structures which mimic the structural and electronic properties of this domain, methods of synthesizing such metal ion-bound chelators are described in detail hereinbelow.

As used herein the metal ion refers to a transition metal ion or any other physiological metal. Examples of such metal ions include but are not limited to Vanadium, Selenium, Molybdenum, Cobalt, Zinc, Copper, Iron, Gallium, Bismuth, Aluminum, Gold, Platinum, Manganese, Chromium, Silver, Antimony, Thalium, Cadmium, Nickel, Mercury, Lead, Magnesium, and Calcium.

It will be appreciated that although each of the transition metal ions described above can be included in the immunizing compositions of this aspect of the present invention, a preferred metal ion is that coordinated within the chelating sequence of the natural metalloprotein. For example, since natural MMPs enclose Zinc at the catalytic domain, a preferred metal ion according to this aspect of the present invention is Zinc or its analogous ions Cobalt or Cademium.

As used herein, the term "chelator" refers to a transition metal chelator, which includes least two atoms capable of coordinating an indicated metal to form a ring.

As is well known in the art, one or more molecules are considered as transition metal chelators if the formation of a cyclic complex of the molecule(s) with an ion of the transition metal results in a "chelate effect". The phrase "chelate effect" refers to the enhanced stability of a complexed system containing the chelate, as compared with the stability of a system that is as similar as possible but contains none or fewer rings. The parameters for evaluating the chelate effect of a chelate typically include the enthalpy and entropy changes ($\Delta H$ and $\Delta S$), according the following equation:

$$\Delta G^0 = \Delta H^0 - T\Delta S^0 = -RT \ln \beta$$

where $\beta$ is the equilibrium constant of the chelate formation and hence represents the chelate effect. Transition metal chelates refer to complexes, which include a transition ion and one or more transition ion chelator(s) complexed therewith, which are characterized by a large $\beta$ value.

Examples of transition metal chelators include, but are not limited to, polyamine molecules such as porphyrins, ethylene diamine and cyclam, which form metal chelates with enhanced chelate effect.

Other examples of metal chelators include diethylenetriamine, di-(monoalkylamino)-alkane, triethylenetetramine, triethylenediamine, tetraethylenepentamine, aminoethylethanolamine, aminoethylpiperazine, pentaethylenehexamine, captopril, penicilamine, N,N'-bis(3-aminopropyl)-1,3-propanediamine, N,N'-Bis-(2-animoethyl)-1,3-propanediamine, 1,7-dioxa-4,10-diazacyclododecane, 1,4,8,11-tetraaza cyclotetradecane-5,7-dione, 1,4,7-triazacyclononane, 1-oxa-4,7,10-triazacyclododecane, 1,4,8,12-tetraazacyclopentadecane, and 1,4,7,10-tetraazacyclododecane. For further discussion on metal chelators by Ross and Frant, Chelometric indicators, titration with the solid state cupric ion selective electrode. (1969) Analytical Chemistry 41:1900.

It will be appreciated that peptide chelators can also be used according to this aspect of the present invention. U.S. Pat. No. 5,679,548 discloses a method of generating such chelators.

In any case as described above the chelating composition is selected based upon the structural and electronic properties of the actual domain in the target polypeptide. Typically, the target polypeptide includes 3 amino acids which provide three contact points required for the transition metal coordination. Representative coordination complex geometries can be tetrahedral, square planar or trigonal depending upon the transition metal ion. In general the mimicking compositions of the present invention are selected based upon the amino acid side chain structure and the geometry of coordination. Typically, amino acids which can coordinate transition metal binding are histidine, arginine, glutamate, cysteine, methionine, tryptophan, serine, threonine and tyrosine, with the first two being preferable.

Histidine, arginine and tryptophan have an amino group that can coordinate a transition metal atom. In Histidine, the amino group is located within a cyclic imidazole ring and hence the lone pair electrons (lpe) of the nitrogen are more available for coordination, as compared with aliphatic amines such as in arginine.

In tryptophane, the amino group is located within an imidazole ring that is conjugated to an aryl ring and hence, its lpe is less available since it participates in the $\pi$ electron system.

Typically, any compound that has an aliphatic or alicyclic amino group (i.e., substituted or unsubstituted) can mimic these amino acid chelating effect, with preference to imidazole-like compounds such as phorphrin. It will be appreciated that Lysine also has an aliphatic amino group, however, at neutral pH conditions the amino group is protonized and hence cannot coordinate transition ions.

Cysteine and Methionine have a sulfur-containing group (i.e., —SH and —S—, respectively), which can also coordinate a transition metal atom. Any compound that includes such a group can exert the same chelating effect.

Tyrosine, Serine and Threonine have an hydroxyl group, either aromatic (Tyrosine) or aliphatic (Serine and Threonine), which exert a less preferable chelating effect, due to possible oxidation of the metal. Any compound which includes such a group or, alternatively, an oxygen-containing group such as ether (—O—), can exert the same chelating effect.

Methods of producing the compositions of the present invention are well known in the art. General metal-insertion protocols are disclosed in Smith, "Porphyrins and Metalloporphyrins, K. M. Smith ed., Elsevier Scientific Publishing Co., New York, (1975).

A specific procedure for synthesizing metalloporphyrins in a low temperature (i.e., 40°) is disclosed in U.S. Pat. No. 6,420,553.

Briefly, hydrophobic or hydrophilic porphyrin compounds having at least one porphyrin ring or rings and optionally bearing various substituent groups can be used as starting materials permitting insertion of a transition metal ion.

The transition metal salts to be complexed with such porphyrin compounds may be any of various salts of the transition metals, described hereinabove, which are able to make at least two formal bonds. The salt of such a transition metals may be any of various inorganic acids, such as hydrochloric acid, sulfuric acid, phosphoric acid, and various organic acids. The transition metal salt is preferably used in a molar excess over the starting material porphyrin.

While conducting the reaction, the starting material porphyrin and the transition metal salt are dissolved each in an independent solvent and the resulting solutions are combined.

The solvent for dissolving the starting material porphyrin is selected according to the hydrophobicity of the porphyrin. A solvent having a high solubilizing power for the porphyrin and capable of providing a homogeneous solution is preferably used. For example, when a hydrophobic porphyrin is reacted, hydrophobic organic solvents are preferably used. Thus, halogenated hydrocarbons, aromatic hydrocarbons, nitriles and the like may be used.

Alternatively, when the starting material porphyrin is hydrophilic, hydrophilic solvents such as water, alcohols, amines, nitrogeneous heterocyclic compounds are preferably used.

The homogeneous solutions, thus prepared, are combined in the presence of a basic substance or basic compound. The presence of a basic substance can be assured, for example by using a basic substance as the solvent when it is an amine or a nitrogeneous heterocyclic compound or by adding a basic substance to the combined solution, or even by using such procedures in combination. The relative amount of the solvent and basic substance can vary.

Examples of basic substances which can be used include, but are not limited to, nitrogen-containing heterocyclic compounds such as pyridine, methylpyridine, dimethylpyridine, diazines, methyldiazines, pyrazine, ethylpyrazine, pyrimidine, piperazine, morpholine; aliphatic amines such as diethylamine, ethylenediamine, tert-butylamine, basic resins; and inorganic bases.

The reaction is preferably effected at 40° C., although lower temperature conditions (i.e., room temperature) can also mediate the reaction.

Once the reaction is complete, the reaction product can be isolated and purified by various procedures such as chromatography, precipitation, recrystallization and the like.

Alternatively, the compositions of the present invention can be commercially obtained such as from Frontier Scientific Porphyrin Products (www.porphyrin.com).

In any case, once the composition of the present invention is obtained, it is used to generate antibodies or antibody fragments thereto.

As used herein the term "antibody", refers to an intact antibody molecule and the phrase "antibody fragment" refers to a functional fragment thereof, such as Fab, F(ab')$_2$, and Fv that are capable of binding to macrophages. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (iv) Fv, defined as a genetically engineered fragment containing the variable region of the light chain and the variable region of the heavy chain expressed as two chains; (v) Single chain antibody ("SCA"), a genetically engineered molecule containing the variable region of the light chain and the variable region of the heavy chain, linked by a suitable polypeptide linker as a genetically fused single chain molecule; and (vi) Peptides coding for a single complementarity-determining region (CDR).

Methods of generating antibodies (i.e., monoclonal and polyclonal) are well known in the art. Antibodies may be generated via any one of several methods known in the art, which methods can employ induction of in vivo production of antibody molecules, screening immunoglobulin libraries or panels of highly specific binding reagents as disclosed [Orlandi D. R. et al. (1989) Proc. Natl. Acad. Sci. 86:3833-3837, Winter G. et al. (1991) Nature 349:293-299] or generation of monoclonal antibody molecules by continuous cell lines in culture. These include but are not limited to, the hybridoma technique, the human B-cell hybridoma technique, and the Epstein-Bar-Virus (EBV)-hybridoma technique [Kohler G., et al. (1975) Nature 256:495-497, Kozbor D., et al. (1985) J. Immunol. Methods 81:31-42, Cote R. J. et al. (1983) Proc. Natl. Acad. Sci. 80:2026-2030, Cole S. P. et al. (1984) Mol. Cell. Biol. 62:109-120].

In cases where the invention compounds are too small to elicit a strong immunogenic response, such antigens (haptens) can be coupled to antigenically neutral carriers such as keyhole limpet hemocyanin (KLH) or serum albumin [e.g., bovine serum albumine (BSA)] carriers (see U.S. Pat. Nos. 5,189,178 and 5,239,078 and Examples 2 of the Examples section). Coupling to carrier can be effected using methods well known in the art; For example, direct coupling to amino groups can be effected and optionally followed by reduction of imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. (See for example, Harlow and Lane, Antibodies: A Laboratory Manual, Cold Spring Harbor Laboratory, New York, 1988, incorporated herein by reference). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment.

Alternatively, antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778.

CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

It will be appreciated that for human therapy or diagnostics, humanized antibodies are preferably used. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Once antibodies are obtained, they may be tested for metalloprotein inhibitory activity. Appropriate assay conditions for metalloprotein inhibition activity are described in Knight et al., FEBS Letters 296(3):263-266 (1992), Cawston et al., Anal. Biochem, 99:340-345 (1979), Cawston et al., Methods in Enzymology 80:771 et seq. (1981); Cawston et al., Biochem. J., 195:159-165 (1981), Weingarten et al., Biochem. Biophys. Res. Comm., 139:1184-1187 (1984) and U.S. Pat. Nos. 4,743,587 and 5,240,958.

Using the methodology described hereinabove, the present inventors were able to produce matrix metalloprotease (MMP) inhibitory antibodies for MMP-2 and MMP-9.

Thus, according to another aspect of the present invention there is provided an antibody or an antibody fragment, which is capable of inhibiting the activity of an MMP. The antibody or antibody fragment of this aspect of the present invention includes an antigen recognition region (antigen binding region) that is capable of binding a structure, which includes a metal ion coordinately bound within a chelator thereof.

As is illustrated in the Examples section which follows, the present inventors have conclusively shown that such an antibody raised against a chelator-metal ion structure present in an MMP is capable of specifically and efficiently inhibiting the activity of an active form of such an enzyme.

A matrix metalloprotease refers to an enzyme which degrades connective tissues and connective tissue components and which includes a catalytic domain having a chelating sequence, such as the zinc-binding motif set forth in HEXXHXXGXXH and a transition metal ion such as Zinc.

Table 1 below, lists a number of vertebrate MMPs, as well as non-vertebrate members, which have been identified in sea urchins, *Caenorhabditis elegans*, soybean, and *Arabidopsis thaliana* and which can be used as targets for the potent inhibitors of this aspect of the present invention.

TABLE 1

| Protein | MMP |
|---|---|
| Collagenase 1 | MMP-1 |
| Gelatinase A | MMP-2 |
| Stromelysin 1 | MMP-3 |
| Matrilysin | MMP-7 |
| Collagenase 2 | MMP-8 |
| Gelatinase B | MMP-9 |
| Stromelysin 2 | MMP-10 |
| Stromelysin 3 | MMP-11 |
| Macrophage elastase | MMP-12 |
| Collagenase 3 | MMP-13 |
| MT1-MMP | MMP-14 |
| MT2-MMP | MMP-15 |
| MT3-MMP | MMP-16 |
| MT4-MMP | MMP-17 |
| Collagenase 4 (*Xenopus*) | MMP-18 |
| (No trivial name) | MMP-19 |
| Enamelysin | MMP-20 |
| XMMP | MMP-21 |
| CMMP | MMP-22 |
| (No trivial name) | MMP-23 |

Since the chelating sequence of MMP includes histidine residues which are imidazole based ligands as described above, the metal chelator utilized for generating MMP neutralizing antibodies according to the teachings of the present invention preferably includes at least two porphyrin-like molecules, which are imidazole-like structures.

A variety of synthetic porphyrins are known in the art. Examples include but are not limited to 5,10,15,20-Tetra(4-pyridyl)porphyrin, 5,10,15,20-Tetra(4-pyridyl)porphyrin, 5,10,15,20-Tetrakis(1-methyl-4-pyridinio)porphyrin tetra(p-toluenesulfonate), 5,10,15,20-Tetrakis(4-trimethylammoniophenyl)porphyrin tetra(p-toluenesulfonate) and 5,10,15,20-Tetrakis(pentafluorophenyl)porphyrin. Such porphyrins are commercially available from Sigma-Aldrich (www.sigmaaldrich.com).

Examples of compositions which can be used to generate the inhibitory antibodies of this aspect of the present invention include, but are not limited to, "capped" porphyrins [Almog, J., et al., J. Am. Chem. 97:226-227 (1975); Almog, J., et al., Tetrahedron 37:3589-3601 (1981); Baldwin, J. E., et al., J. Chem. Soc., Dalton Trans. pp. 1739-1746 (1984)], "bridged" porphyrins [Battersby, A. R., et al., J. Chem. Soc., Chem. Comm. pp. 879-891 (1976); Battersby, A. R., et al., Tetrahedron Lett. 3169-3172 (1978)], "picket fence" porphyrins [Collman, J. P., et al., J. Am. Chem. Soc. 95:7868-7870 (1973); Collman, J. P., et al., J. Am. Chem. Soc. 97:1427-1439 (1975)], "pocket" porphyrins [Collman, J. P., et al., Inorg. Chem. 22:1427-1432 (1983)], "basket-handle" porphyrins [Momenteau, M., et al., Nouv. J. Chim. 3:77-99 (1979); Momenteau, M., et al., J. Mol. Catal. 7:315-320 (1980); Momenteau, M., et al., J. Chem. Soc. Perkins Trans. 1:189-196 (1983)], "gyroscope" porphyrins [Lecas, A., et al., Tetrahedron Lett. pp. 1019-1022 (1985); Boitrel, B., et al., J. Chem. Soc. Chem. Comm. pp. 1820 (1985)], "cyclophane" porphyrins [Diekmann, H., et al., J. Am. Chem. Soc. 93:4068-4070 (1971); Traylor, T. G., et al., J. Am. Chem. Soc. 107:604-614 (1985)], and "jelly-fish" type porphyrins [Uemori, Y., et al., Inorg. Chem. 28:1690-1694 (1989)].

As is mentioned hereinabove, one specific use for the antibodies of the present invention is prevention or treatment of diseases associated with imbalanced or abnormal activity of metalloproteins such as metalloproteases.

Examples of such disease include, but are not limited to, arthritic diseases, such as osteoarthritis (OA), rheumatoid arthritis (RA), septic arthritis, soft tissue rheumatism, polychondritis and tendonitis; metastatic tumors, periodontal diseases; corneal ulceration, such as induced by alkali or other burns, by radiation, by vitamin E or retinoid deficiency; glomerular diseases, such as proteinuria, dytrophobic epidermolysis bullosa; bone resorption diseases, such as osteoporosis, Paget's disease, hyperparathyroidism and cholesteatoma; birth control through preventing ovulation or implantation; angiogenesis relating to tumor growth or to the neovascularization associated with diabetic retinopathy and macular degeneration; coronary thrombosis associated with atherosclerotic plaque rupture; pulmonary emphysema, wound healing and HIV infection.

Thus, according to another aspect of the present invention there is provided a method of inhibiting matrix metalloprotease activity in a subject in need thereof.

Preferred individual subjects according to the present invention are mammals such as canines, felines, ovines, porcines, equines, bovines, humans and the like.

The method includes providing to the subject a therapeutically effective amount of the MMP inhibitor of the present invention (i.e., the antibody or antibody fragments, described hereinabove).

As is further detailed hereinbelow, the MMP inhibitor can be provided via direct administration (e.g., oral administration or injection) or it can be expressed from a polynucleotide construct administered to target cells of the individual.

The MMP inhibitors of the present invention can be provided to an individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

As described hereinabove, the antibody inhibitors of the present invention can be expressed from a nucleic acid construct.

It will be appreciated that polynucleotides encoding the antibodies of the present invention preferably further encode a signal peptide which allows secretion or trafficking of the antibodies into a subcellular or extracellular localization of interest. For example, when the target metalloprotein is an MMP, a secretory signal peptide is preferably conjugated inframe to the polynucleotide encoding antibody segment.

It will be further appreciated that recombinant single-chain Fv (ScFv) fragments may be preferably expressed because of their considerably less complicated structure as compared to whole antibody molecules. As described hereinabove ScFvs are proteins consisting of the $V_L$ and $V_H$ antibody polypeptide chains synthesized as a single chain with the carboxyl terminus of $V_L$ linked by a peptide bridge to the amino terminus of $V_H$ Methods for recombinantly producing these peptides are well known in the art [see Bird et al., Science 242:423-426 (1988); Huston et al., Proc. Nat'l Acad. Sci. USA 85:5879-5883 (1988); and de Kruif et al., J. Mol. Biol. 248:97-105 (1995)]. According to embodiments of this aspect of the present invention, following immunization with the compounds of the present invention, splenic, mRNA is harvested from the immunized animal and used to produce a cDNA library in a bacteriophage which displays the ScFv fragments. Phage particles are then screened to determine those that interact specifically and preferably with the activated form of the metallop[rotein of interest. ScFv segments are recovered from these phage particles, and cloned into an expression construct (see U.S. Pat. No. 5,800,814).

The nucleic acid constructs of this aspect of the present invention can be administered to target cells of the individual subject (i.e., in-vivo gene therapy).

Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

To enable cellular expression of the antibodies or antibody fragments of the present invention, the nucleic acid construct of the present invention further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any available promoter can be used by the present methodology. In a preferred embodiment of the present invention, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The constructs of the present methodology preferably further include an appropriate selectable marker and/or an origin of replication. Preferably, the construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element (s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide or antibody from a host cell in which it is placed. Preferably the signal sequence for this purpose is a mammalian signal sequence. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Preferred modes for executing gene therapy protocols are provided in Somia and Verma [(2000) Nature Reviews 1:91-99], Isner (2002) Myocardial gene therapy. Nature 415:234-239; High (2001) Gene therapy: a 2001 perspective. Haemophilia 7:23-27; and Hammond and McKirnan (2001) Angiogenic gene therapy for heart disease: a review of animal studies and clinical trials. 49:561-567.

Because of the ability of the antibodies of the present invention to differentially recognize the activated form of metalloprotein (see Examples 5 and 6 of the Examples section), they can be used as potent diagnostic and prognostic tools, such as by monitoring MMP activity in a biological sample [i.e., any body sample such as blood (serum or plasma), sputum, ascites fluids, pleural effusions, urine, biopsy specimens, isolated cells and/or cell membrane preparation]. This is of special significance when evaluating the metastatic features of cancer cells, wherein imbalanced activation of MMPs facilitate tumor invasion. Likewise, the antibodies of the present invention can be used in monitoring therapeutic dosage of MMP inhibitors. For such applications the antibodies of the present invention are preferably labeled with each of any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241.

It will be appreciated that such detection methods can also be used for high throughput screening of novel MMPs. Briefly, multiple biological samples can be contacted with the antibodies of the present invention, where activated MMPs can bind thereto. Measures are taken to use biological samples, which include activated MMPs such as those derived from tumor cell-lines. Typically, a radioactive label is used to reduce the assay volume.

Alternatively, the antibodies of the present invention can be used to purify active metalloenzymes from biological samples.

Numerous protein purification methods are known in the art. For example, the antibodies or antibody fragments of the present invention can be used in affinity chromatography for isolating the metalloenzymes. Columns can be prepared where the antibodies are linked to a solid substrate, e.g., particles, such as agarose, Sephadex, and the like, and the biological sample, such as a cell lysate may be passed through the column, the column washed, followed by increasing concentrations of a mild denaturant, whereby the purified metalloenzyme will be released.

The antibodies or fragments thereof generated according to the teachings of the present invention can be included in a diagnostic or therapeutic kit. Antibodies or antibody fragments can be packaged in a one or more containers with appropriate buffers and preservatives and used for diagnosis or for directing therapeutic treatment.

Thus, the antibodies or fragments thereof can be each mixed in a single container or placed in individual containers. Preferably, the containers include a label. Suitable containers include, for example, bottles, vials, syringes, and test tubes. The containers may be formed from a variety of materials such as glass or plastic.

In addition, other additives such as stabilizers, buffers, blockers and the like may also be added. The antibodies of such kits can also be attached to a solid support, such as beads, array substrate (e.g., chips) and the like and used for diagnostic purposes. The kit can also include instructions for determining if the tested subject is suffering from, or is at risk of developing, a condition, disorder, or disease associated with expression of an MMP of interest.

The present invention also provides a novel approach for qualifying specificity of antibodies to metal ion and chelators thereof by determining conformational changes and/or electronic changes in binding of the metal ion to the chelator thereof following binding of the antibody.

Determining conformational and electronic changes in binding of the metal ion to the chelator thereof following binding of the antibody according to this aspect of the present invention can be effected by x-ray absorption spectroscopy (XAS) studies. XAS refers to the oscillatory structure in the X-ray absorption coefficient above an X-ray absorption edge of a target element. This structure represents a unique signature of a given material, which depends on the detailed atomic structure, electronics, and vibrational properties of the material. A characteristic XAS spectrum consists of the X-ray Absorption Near Edge Spectra (XANES) and the Extended X-ray Absorption Fine Structure (EXAFS) regions. The XANES include information about the oxidation state of the metal ion and its geometry and the analysis of the EXAFS region provides the atomic structure around a given metal ion including the average bond distances, mean square variation in distance, coordination numbers and the identity of the atoms around the metal ion.

Typically, the goal of X-ray absorption studies of proteins has been the investigation of the local atomic environment, within few nearest neighboring shells, around the element of interest. The X-ray absorption cross-section measured in the energy range from the absorption edge energy of the element through ca. 1000 eV past it provides the information about both the structural and electronic properties of the absorber. EXAFS is a valuable technique for structural elucidation of a variety of metal sites in metalloproteins (Scott see above ref). The high-resolution structural information that can be obtained by XAS studies makes it an advantageous tool to monitor active site zinc coordination and electronics in metal binding proteins such as MMPs during different stages of the activation and inhibition processes (Kleifeld Supra). It will be appreciated that XAS is the only spectroscopic tool available to date that can probe directly the otherwise spectroscopically silent zinc ion. Additional details on EXAFS are provided by Scott, R. A. (1985) Methods in Enzymology, 117.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Preparation of Monoclonal Antibodies Against the MMP-2 Active Site

For the production of a specific monoclonal antibody against the electronic and physical features of the MMP-2 active site synthetic haptens (FIG. 3) with an analogue structure to the MMP-2 active site, i.e., a zinc ion coordinated to three histidines and a water molecule (Kleifeld et al., 2001), were synthesized and further used for mice immunization.

Material and Experimental Methods

Synthesis of Co-TCPP and Zn-TCPP haptens—The tetra-carboxy phenyl porphyrin Co(II) (Co-TCPP) and the tetra-carboxy phenyl porphyrin Zn(II) (Zn-TCPP) haptens were synthesized as follows: 63 mM of either $Co(OAc)_2 \cdot 4H_2O$ or $Zn(OAc)_2 \cdot 2H_2O$ in a solution containing methanol and acetic acid at equal concentrations were added to 6.3 mM TCPP. The mixtures were heated for 30 min at 60° C. during which the organic solvents evaporated. The residues were dissolved in the same methanol/acetic acid solution and purified using a silica column [DC Scientific, Ohaio Valee, Kelton, Pa. 19346, USA. See Harada, A. et al, Photochemistry and Photobiology (1999) 70, 298-302]. Purified fractions were further evaporated and yielded the Co-TCPP or Zn-TCPP haptens as brown-purple or purple sediments, respectively. The identity of the sediments was further confirmed using mass spectrometry.

Gelatin zymography—For substrate zymography, a purified protein sample was loaded on a 12% SDS-PAGE containing 0.5 mg/ml gelatin. Activity assay was conducted as described elsewhere (Gogly et al., 1998).

Conjugation of haptens to carrier proteins—The Co-TCPP and Zn-TCPP haptens (4.6 μmole each) were dissolved in 475 μl of dimethylformamide (DMF) and activated for 1 hr at room temperature (RT) by 3.2 μmole of carbonyldiimmidazole (CDI, Fluka, 21860, Sigma-Aldrich Israel Ltd. Rehovot, Israel). Activated haptens were added to cold solutions of 2.5 mg/ml bovine serum albumin (BSA) or of 2.5 mg/ml keyhole limpet hemocyanin (KLH), both in 0.1 M $NaHCO_3$, pH 8. Haptens were stirred for 3 hours at 4° C. and for an additional 1 hour at RT. Hapten conjugates were dialyzed extensively in a solution containing 0.1 M $NaHCO_3$, pH 8 and 3×PBS at a molar concentration of 0.5 mM and diluted to a final concentration of 1 mg/ml and 0.6 mg/ml for Co-TCPP-BSA and Co-TCPP-KLH, respectively, and to a final concentration of 1 mg/ml for both Zn-TCPP-BSA and Zn-TCPP-KLH. For hapten density (Hd) determination hapten conjugates were diluted (1:50) in phosphate buffered saline (PBS) and absorbance was measured at 431 nm. Hapten density per carrier molecule was calculated according to the estimated molar concentration.

Immunization of mice against the TCPP haptens—Mice were immunized by a foot pad injection of 50 μg haptens conjugated to KLH. Following two boost injections in two weeks intervals mice were eyebled to assess antibody titer. One month following the second boost injection a tail vein injection was given (50 μg in PBS) and 3 days later the spleen was fused with poly ethylene glycole (PEG) myeloma cell line to produce hybridomas. Hybridomas were cloned into 96-well plates and screened against hapten conjugates by immunoabsorbent ( ) assay (ELISA) essentially as described elsewhere [Engvall E. and Pece A. J. (1978) Scand. J. Immunol. 8, Suppl. 7].

Purification of monoclonal antibodies—Ascites samples were mixed with an equal volume of $(NH_4)_2SO_4$ and centrifuged for 20 min at 10,000 rpm at 4° C. The pellet was re-suspended in PBS, incubated for 1 hour and dialyzed for 4 hours. Monoclonal antibodies were further purified by protein G Sepharose column (Pharmacia, 17-0618-01, Rehovot, Israel) according to manufacturer's instructions. Purified antibodies were dialyzed again in the same solution for 4 hours and antibody concentration was determined by the absorption at 280 nm.

Experimental Results

The production of monoclonal antibodies against the electronic and physical features of MMP-2—In order to produce specific antibodies that would recognize the electronic and physical features of the MMP-2 catalytic site synthetic haptens corresponding to the catalytic active site were synthesized. In these haptens the cobalt (Co) or zinc (Zn) atoms are linked to the tetra-carboxy phenyl porphyrin molecule (Co-TCPP or Zn-TCPP, respectively) as illustrated in FIG. 3. Prior to mice immunization the haptens were conjugated to bovine serum albumin (BSA) or keyhole limpet hemocyanin (KLH).

Two groups of mice were immunized with Co-TCPP or Zn-TCPP, conjugated to KLH. The serum titer was measured from mice eyebleed 7-10 days following the second and third hapten-boost injection. While mice immunized with the Co- TCPP hapten exhibited a sufficient serum titer of 1:20,000, mice immunized with the Zn-TCPP hapten exhibited a very low and insufficient titer (not shown). Three days following the third boost injection the spleen was removed and fused with myeloma cells. One hundred and twenty clones secreting antibodies were obtained.

These results demonstrate that the Co-TCPP hapten, but not the Zn-TCPP hapten, is stable and suitable for antibody production. These results could be explained by destabilization of the water-zinc bond of the Zn-TCPP hapten in vivo.

Example 2

Identification and Classification of Monoclonal Antibodies

Mononclonal antibodies were identified and classified by their affinity and competition to conjugated haptens.

Materials and Experimental Methods

Affinity of the monoclonal antibody to conjugated haptens—Microtiter plates (Maxi Immunoabsorp, Nunc, Rehovot, Israel) were coated for 1 hour with 3 µg/ml of Hapten conjugates in PBS, blocked for 1 hour in 1% BSA/PBS and further subjected to 1 hour incubation with various concentrations of monoclonal antibodies. Coated plates were then washed three times in 0.04% Tween-20 (Sigma, rehovot, Israel) in PBS followed by 1 hour incubation with a secondary goat anti mouse peroxidase conjugated antibody (Jackson ImmunoResearch Laboratories Inc., Tel-Aviv, Israel). Plates were then washed again in PBS and peroxidase reactions were developed in a solution containing 0.028M citric acid, 0.044 M $Na_2HPO_4$, 1 mg/ml ABTS (2,2, azino-bis(3-Ethylbenthiazoline-6-sulfonic acid) and 30% $H_2O_2$.

Characterization of antibody subclasses—Monoclonal antibodies (1 µg in 50 µl) were added to hapten-coated microtiter plates and incubated for 1 hour at RT. Plates were then washed in PBS containing 0.04% Tween-20 and various types of secondary peroxidase conjugated antibodies ($IgG_1$, $IgG_{2a}$, $IgG_{2b}$, $IgG_{g3}$, IgM) were added for 1 hour incubation. Antibody-bound plates were then washed in PBS and peroxidase reactions were developed as described hereinabove.

Experimental Results

Hybridoma screening—Isolated hybridomas were grown for one week. Hybridoma conditioned media were then analyzed for ability to bind a solid phase bound hapten antigen. Fifty positive hybridomas (out of 120) were further analyzed for the ability of the antigen to inhibit antibody binding to the immunizing hapten conjugated to BSA. This analysis resulted in 17 hybridomas in which 50% inhibition was achieved in less than $10^{-6}$M hapten concentration (data not shown).

Antibody subclasses—Antibody-secreting hybridomas were classified to subclasses by binding to $IgG_1$, $IgG_{2a}$, $IgG_{2b}$, $IgG_{g3}$, or IgM secondary antibodies. Thirteen out of 17 hybridomas were identified as monoclonal antibodies of them one was IgM and 12 were IgGs (not shown). Four hybridomas with the lowest value for 50% inhibition (e.g., lower than $10^{-7}$ M) were further subcloned and tested for MMP-2 inhibition. Among them the antibody with the best inhibition effect (Co-TCPP13e11) was propagated as ascites.

These results demonstrate the production of a specific monoclonal antibody targeted at the Co-TCPP hapten.

Example 3

Characterization of MMP-2 Monoclonal Antibody

To further characterize the Co-TCPP monoclonal antibody competitive assays with hapten competitors and immunoprecipitation assays were performed.

Materials and Experimental Methods

Competitive assay—Monoclonal antibodies (at 50% binding concentration) were incubated for 1 hour with the TCPP, Co-TCPP, Zn-TCPP, Zn-TPP hapten competitors and were then transferred to hapten-coated microtiter plates as described in Example 2 hereinabove. The dissociation constant required to attain 50% binding was determined.

Immuno precipitation—Protein A beads Pharmacia, Rehovot, Israel were washed in PBS according to manufacturer instructions. Ten µg of monoclonal antibody in 300 µl PBS were added to ~30 µl of washed protein A beads and incubated over night at 4° C. Protein A-bound antibodies were then washed three times in PBS and further incubated for 3 hours at RT with 1 µg of MMP-2 catalytic domain [MegaPharm (Oncogene Research Products), Hod-Hasharon, Israel, Cat. #PF023] continuous shaking. Following incubation the mixture was centrifuged for 2 min at 3000 rpm and pellet and supernatant phases were analyzed on a 12% SDS-PAGE gel.

Kinetic assays using a fluorogenic substrate—The inhibitory effect of the antibodies of the present invention on the hydrolysis of the Mca-Pro-Leu-Gly-Leu-Dpa-Ala-Arg-$NH_2$ fluorogenic substrate (synthesized in the laboratory of Pof. Fridkin at the Weizmann Institute) by the MMP-2 catalytic domain protein was measured as described elsewhere (Netzel-Arnett et al., 1991). Briefly, MMP-2 samples (200 nM) were added to the fluorogenic substrate at a concentration range of 0.4-50 µM in a final volume of 200 µL. The reaction was performed at 37° C. and enzyme activity was monitored every 8 seconds along 30 minutes by measuring the fluorescence intensity (emission at 390 nm, excitation at 340 nm) using the SPECTRAFluor Plus apparatus (TECAN, Pharatop, Tel-Aviv, Israel). The V, was calculated for each substrate concentration by the linear part of each kinetic curve and the kinetic parameters ($K_M$ and $V_{MAX}$) were calculated from the Lineveawer-Burk plot.

Experimental Results

The affinity of the monoclonal antibody to Co-TCPP hapten—The Co-TCPP13e11 monoclonal antibody was characterized by its affinity to the immunizing Co-TCPP hapten. Serial dilutions of the purified antibody were added to Co-TCPP-coated microtiter plates. The $IC_{50}$ value, which corresponds to the antibody dilution required for 50% binding, was calculated from the titration curve (FIG. 4) and was found to be ~20,000.

Competitive assay revealed antibody specificity towards the immunizing hapten—To determine whether the antibody binds specifically to the immunizing hapten, the monoclonal antibody was incubated with Co-TCPP, Zn-TCPP, TCPP, and Zn-TPP and titration curves were plotted against hapten concentrations (FIG. 5). The dissociation constants, i.e., the concentration which results in 50% binding of the antibody to the hapten, were $9 \times 10^{-8}$ M, $1 \times 10^{-5}$ M, $2 \times 10^{-5}$ M, and $3 \times 10^{-5}$ M for Co-TCPP, Zn-TCPP, TCPP, and Zn-TPP respectively. These values demonstrate the high specificity of the antibody towards the immunizing hapten (Co-TCPP).

Specific inhibition of MMP-2 and MMP-9 activity by the monoclonal antibody—To determine whether Co-TCPP13e11 monoclonal antibody can specifically inhibit the MMP proteins the hydrolysis of the fluorogenic substrate was measured in the presence of the antibody. The kinetic parameters of the inhibition assay (i.e., Ki) were 24 µM and 13 µM for the MMP-2 catalytic domain and MMP-9 full-length enzyme, respectively. Interestingly, at all antibody concentrations the Lineweaver-Burk curves exhibited a single and common intersect point on the Y axis (FIGS. 6a-b). These results suggest that the monoclonal antibody inhibited the MMP-2 and MMP-9 enzymes in a competitive manner.

The selectivity of the monoclonal antibody towards MMPs was further examined by testing its inhibitory effect on a different zinc—dependent enzyme, the Thermoanaerobacter brockii alcohol dehydrogenase (TbADH). This enzyme catalyses the reversible oxidation of secondary alcohols to the corresponding ketones using $NADP^+$ as a cofactor (Korkhin et al., 1998). The catalytic zinc in TbADH is coordinated to histidine, cysteine, aspartate, and glutamate in a tetraheder configuration. Incubation of the monoclonal antibody with TbADH did not affect the enzyme activity (data not shown).

These results further suggest that the monoclonal antibody recognizes the exposed imidazole-based histidine protein residues, which are coordinated to the catalytic zinc ion in MMP's (Morgunova et al., 1999; Kleifeld et al., 2001) and not necessarily the zinc ion itself.

Immuno precipitation (IP) analyses with the monoclonal antibody revealed high specificity towards MMP-2 catalytic domain—To further verify that the monoclonal antibody inhibited the activity of the various MMPs by directly interacting with their catalytic site, a series of immuno-precipitation (IP)— based experiments were conducted. Briefly, the monoclonal antibody was associated with protein A beads and the MMP-2 catalytic domain enzyme was added for three hours incubation. Following centrifugation the beads-containing phase (i.e., the pellet) and the beads-free phase (i.e., the soluble) were analysed on an SDS-PAGE gel. When the MMP-2 catalytic domain was incubated with antibody-free protein A beads the MMP-2 was contained within the soluble phase (FIG. 7a, lane 1) but not the pellet phase (FIG. 7a, lane 2). In addition, when the monoclonal antibody was incubated with protein A beads the antibody was included in the pellet phase (FIG. 10a, lane 4) but not the soluble phase (FIG. 10a, lane 3). These results ruled out the possibility of a direct association between the MMP-2 enzyme and protein A beads. On the other hand, the MMP-2 enzyme was found in the pellet phase when incubated with pre-associated antibody-protein A beads (FIG. 7a, lanes 5 and 6). To rule out the possibility that the enzyme and antibody associated to form aggregates directly they were co-incubated in the absence of protein A beads. As shown in FIG. 7a (lane 9) the soluble phase contained both the antibody and the enzyme. To further study the specificity of the antibody to MMP-2, the pre-associated antibody-bound beads were incubated with the non-relevant RNA-helicase Dead Box Protein A (DbpA). No specific binding was observed in the pellet phase (FIG. 7a, lanes 7 and 8) indicating lack of specific interaction between the antibody and DbpA. Similar results were obtained with other non-relevant proteins (e.g., the C-terminal cytoplasmic domain of gliotactin, data not shown).

Altogether, these results demonstrate that the monoclonal antibody binds the MMP-2 catalytic domain in a highly specific way and form a stable complex.

The zinc ion is necessary for antibody binding—The zinc ion of the MMP-2 catalytic domain was chelated using the ortho-phenanthroline [Maret W., Makinen, M. W., JBC, 266, 20636-44 (1991)] and the enzyme was further incubated with pre-associated antibody-protein A beads. As shown in FIG. 7b (lanes 1 and 2) the monoclonal antibody did not bind the zinc-free MMP-2 catalytic domain. These results demonstrate that the zinc ion in the enzyme is critical for antibody binding. In addition, incubation of the antibody-MMP-2 complex with the hydroxamate-based high affinity MMP inhibitor, GM-6001 (Bendeck et al., 1996), did not affect the integrity of the complex (FIG. 7c). These results further suggest that the antibody forms a tight, and irreversible complex with the active site of the MMP-2 enzyme.

Altogether, these results demonstrate that the Co-TCPP monoclonal antibody can specifically inhibit the MMP-2 active site. Moreover, these results suggest that the antibody initially recognizes the imidazole-based histidine zinc-ligands within the MMP catalytic site, and then binds to the catalytic metal atom.

Example 4

X-Ray Absorption Spectroscopy (XAS) Studies

XAS refers to the oscillatory structure in the X-ray absorption coefficient above an X-ray absorption edge of a target element. This structure represents a unique signature of a given material, which depends on the detailed atomic structure, electronics, and vibrational properties of the material. A characteristic XAS spectrum consists of the X-ray Absorption Near Edge Spectra (XANES) and the Extended X-ray Absorption Fine Structure (EXAFS) regions. The XANES include information about the oxidation state of the metal ion and its geometry and the analysis of the EXAFS region provides the atomic structure around a given metal ion including the average bond distances, mean square variation in distance, coordination numbers and the identity of the atoms around the metal ion.

Materials and Experimental Methods

Sample preparation for XAS studies—Pro-MMP-2 (Fridman et al., 1992; obtained from Prof. R. Fridman, Wayne State University, Detroit, USA) was activated by 4-aminophenylmercuric acetate (APMA) as described elsewhere (Kleifeld et al., 2001). The enzyme and the monoclonal antibody were concentrated by ultrafiltration using a Millipore Centricon-10 device (Bedford, Mass., USA) to a final concentration of 0.1 mM and 0.2 mM, respectively. Samples were loaded into copper sample holders (10×5×0.5 mm made in the technical service unit at the Weizmann Institute) covered with Mylar tape and were frozen immediately in liquid nitrogen. Frozen samples were mounted inside a Displex closed-cycle helium cryostat (Brookhaven Laboratory, New-York, USA).

XAS data collection, processing and analysis—XAS studies were performed as described elsewhere (Kleifeld et al., 2001). Briefly, the incident beam intensity, $I_0$, was recorded using an ionization chamber (Brookhaven Laboratory, New-York, USA) and the fluorescence intensity, $I_F$, was recorded using a 13-element germanium detector (Crambera, Calif., USA).

EXAFS fitting—Model data for the fitting procedure were constructed by extracting the catalytic zinc site coordinates (in a radius of 5 Å) from the structure of a small molecule, WABKIT, that contains a zinc ion coordinated to three histidines, one oxygen and one sulfur, obtained from the Protein Data Bank (PDB, http://www.rcsb.org/pdb/). The theoretical photoelectron scattering amplitudes and phase shifts were calculated using the computer code FEFF7 (Rehr et al., 1991; Zabinsky et al., 1995). The theoretical XAFS signal was fitted to the experimental data using the nonlinear least squares fitting method, implemented in the program FEFFIT (Stern et al., 1995).

Experimental Results

The structure of the MMP-2 catalytic site is changed upon binding of monoclonal antibodies—The local structure of the catalytic zinc ion in the recombinant, full-length human MMP-2 enzyme in its latent (i.e., pro-enzyme), active, and monoclonal antibody-inhibited states were studied using XAS. The pro-enzyme edge spectrum displayed three distinct peaks at 9668, 9713 and 9738 electron volt (eV) and a typical cleft at 9725 eV. Activation of MMP-2 resulted in a slight increase in peak intensity at 9668 eV. On the other hand, the inhibition of MMP-2 by the monoclonal antibody resulted in a higher peak at 9668 eV, an additional peak at 9680 eV (FIG. 8a, arrow 1) and the absence of evident cleft at 9730 eV (FIG. 8a, arrow 2). In addition, a distinct shift of 0.86 eV to higher energy is observed between the active and the inhibited enzyme (FIG. 8b). These spectral differences in XANES demonstrate local conformational changes in the metal atom of the active site of MMP-2 upon binding of the antibody.

Fitting analysis of MMP-2 active site—In order to further elucidate the conformational changes occurring in the active site following antibody binding an EXAFS fitting analysis was performed. FIG. 9 demonstrates the fitting results of the experimental data to theory. Data are presented as the radial distribution from the main absorber (the zinc ion) and the nearest coordination shells. The F.T. magnitude indicates the peak intensities in arbitrary numbers. These results are consistent with the penta coordination of the zinc ion with three Zn—N at 2.07 Å, one Zn—S at 2.49 Å, and one Zn—O or Zn—N at 1.96 Å and further demonstrate that the antibody binds directly to the catalytic zinc ion via one Zn—S and one Zn—O or Zn—N ligands.

Altogether these results demonstrate that the monoclonal antibody binds the catalytic zinc ion.

Example 5

Complimentary Assays Support the Exafs Results

To determine whether the antibody can be removed from the MMP-2 catalytic site by the cleavage of the Zn—S bond (Van Wart and Birkedal-Hansen, 1990) the antibody-MMP-2 complex was incubated with APMA.

Experimental Results

The antibody-MMP-2 association is relatively stable—The antibody-MMP-2 complex was subjected to APMA treatment as described elsewhere (Kleifeld et al., 2001) and the soluble and pellet phases were further analyzed by IP on an SDS-PAGE gel. As shown in FIG. 10, only a small portion of the MMP-2 enzyme was released from the antibody-enzyme complex.

These results demonstrate a relatively low accessibility of the APMA reagent to the catalytic site of the enzyme due to antibody shielding.

Example 6

Anti MMP-2 Monoclonal Antibody Blocks Pericellular Proteolysis of Highly Invasive Fibrocarcinoma Cells The ability of anti-MMP2 monoclonal antibody of the present invention to inhibit pericellular proteolytic activity generated by highly invasive fibrocarcoma cancer cells (HT1080), was assayed by in situ zymography assay.

Materials and Experimental Procedures

Cells, buffers and growth conditions—HT1080 cells were obtained from the American type culture collection (ATCC, Catalog No. CRL-12011). Cells were grown in Dulbecco's modified Eagle's medium with 4 mM L-glutamine adjusted to contain 1.5 g/L sodium bicarbonate and 4.5 g/L glucose and supplemented with 0.1 mM nonessential amino acids, 90%; fetal bovine serum, 10% at 37° C.

In situ zymography assay—HT1080 were embedded in fully conjugated fluorescent matrigel and in-situ zymography assay was effected essentially as described by Wang et al. Comp Hepatol. 2004 Jan. 14; 3 Suppl 1:S20; and Nakada Am J Pathol. 1999 February; 154(2):417-28.

Experimental Results

HT1080 cells serve as a good model for matrix invasion since they contain MT1-MMPs MMP-2, MMP-9, and TIMPS. Cells were incubated in the presence (FIG. 11b) or absence (FIG. 11a) of anti MMP-2 monoclonal antibody described above DAPI stained and subjected to an in situ zymography assay. As is clearly shown in FIGS. 11a-b, in the absence of anti MMP2 antibody (FIG. 11a), MMP pericellular proteolysis appeared as green intensity around the cell membrane. However upon addition of the antibody, this pattern disappeared, demonstrating that the mAb inhibits the proteolytic activity of MMPs generated from these highly invasive cancer cells with a Ki of 1 μM. These results therefore suggest that the mAb binds and inhibits active MMPs within the pericellular space.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCE LIST

Additional References are Cited in the Text

1. Nagase, H. and Woessner, J. F. Jr. (1999). Matrix metalloproteiases. Minireview. J. Biol. Chem. 274: 21491-21494.
2. Bode, W., Fernandez-Catalan, C., Nagase, H., and Maskos, K. (1999). Endoproteinase-protein inhibitor interactions. APMIS107, 3-10.
3. Bode, W., Fernandez-Catalan, C., Tschesche, H., Grams, F., Nagase, H., and Maskos, K. (1999). Structural properties of matrix metalloproteinases. Cell. Mol. Life. Sci. 55, 639-652.
4. Borkakoti, N. (1998). Matrix metalloproteases: variations on a theme. Prog. Biophys. Mol. Biol. 70, 73-94.
5. Brown, S., Bernardo, M. M., Li, Z. H., Kotra, L. P., Tanaka, Y., Fridman, R., and Mobashery, S. (2000). Potent and Selective Mechanism-Based Inhibition of Gelatinases. J. Am. Chem. Soc., 122, 6799-6800.
6. Fridman, R., Fuerst, T. R., Bird, R. E., Hoyhtya, M., Oelkuct, M., Kraus, S., Komarek, D., Liotta, L. A., Berman, M. L., and Stetler-Stevenson, W. G. (1992). Domain structure of human 72-kDa gelatinase/type IV collagenase. Characterization of proteolytic activity and identification of the tissue inhibitor of metalloproteinase-2 (TIMP-2) binding regions. J. Biol. Chem. 267, 15398-405.

7. Gogly, B., Groult, N., Hornebeck, W., Godeau, G., and Pellat, B. (1998). Collagen Zymography as a Sensitive and Specific Technique for the Determination of Subpicogram Levels of Interstitial Collagenase. Anal. Biochem. 255, 211-216.
8. Gomez, D. E., Alonso, D. F., Yoshiji, H., and Thorgeirsson, U. P. (1997). Tissue inhibitors of metalloproteinases: structure, regulation and biological functions. Eur. J. Cell. Biol. 74, 111-122.
9. Henriet, P., Blavier, L., and Declerck, Y. A. (1999). Tissue inhibitors of metalloproteinases (TIMP) in invasion and proliferation. APMIS 107, 111-119.
10. Kleifeld, O., Kotra, L. P., Gervasi, D. C., Brown, S., Bernardo, M. M., Fridman, R., Mobashery, S., and Sagi, I. (2001). X-ray Absorption Studies of Human Matrix Metalloproteinase-2 (MMP-2) Bound to a Highly Selective Mechanism-based Inhibitor. Comparison with the latent and active forms of the enzyme. J. Biol. Chem. 276, 17125-17131.
11. Korkhin, Y., Kalb(Gilboa), A. J., Peretz, M., Bogin, O., Burstein, Y., and Frolow, F. (1998). NADP-dependent Bacterial Alcohol Dehydrogenases: Crystal Structure, Cofactor-binding and Cofactor Specificity of the ADHs of *Clostridium beijerinckii* and Thermoanaerobacter brockii. J. Mol. Biol. 278, 967-981.
12. Morgunova, E., Tuuttila, A., Bergmann, U., Isupov, M., Lindqvist, Y., Schneider, G., and Tryggvason, K. (1999). Structure of Human Pro-Matrix Metalloproteinase-2: Activation Mechanism Revealed. Science 284, 1667-1670.
13. Bode, W., Fernandez-Catalan, C., Tschesche, H., Grams, F., Nagase, H., and Maskos, K. (1999). Structural properties of matrix metalloproteinases. Cell. Mol. Life. Sci. 55, 639-652.
14. Netzel-Arnett, S., Mallya, S. K., Nagase, H., Birkedal-Hansen, H., and Van Wart, H. E. (1991). Continuously recording fluorescent assays optimized for five human matrix metalloproteinases. Anal. Biochem. 195, 86-92.
15. Rehr, J. J., Mustre de leon, J., Zabinsky, S. I., and Albers, R. C. (1991). J. Am. Chem. Soc. USA 113, 5135-5138.
16. Reponen, P., Sahlberg, C., Huhtala, P., Hurskainen, T., Thesleff, I., and Tryggvason, K. (1992). Molecular cloning of murine 72-kDa type IV collagenase and its expression during mouse development. J. Biol. Chem. 267, 7856-7862.
17. Stern, E. A., Newville, M., Ravel, B., Yacoby, Y., and Haskel, D. (1995). The UWXAFS analysis package: philosophy and details. Physica B 208/209, 117-122.
18. Van Wart, H., and Birkedal-Hansen, H. (1990). The Cysteine Switch: A Principle of Regulation of Metalloproteinase Activity with Potential Applicability to the Entire Matrix Metalloproteinase Gene Family. Proc. Natl. Acad. Sci. USA 87, 5578-5582.
19. Will, H., Atkinson, S. J., Butler, G. S., Smith, B., and Murphy G. (1996). The soluble catalytic domain of membrane type 1 matrix metalloproteinase cleaves the propeptide of progelatinase A and initiates autoproteolytic activation. J. Biol. Chem. 271, 17119-17123.
20. Zabinsky, S. I., Rehr, J. J., Ankudinov, A., Albers, R. C., and Eller, M. J. (1995). Multiple-scattering calculations of x-ray-absorption spectra. Phys. Rev. B 52, 2995-3009.

What is claimed is:

1. An isolated antibody comprising an antigen recognition region which binds Cobalt(II)-tetra-carbozyl phenyl porphyrin (Co-TCPP) or Zinc (II)-tetra-carboxy phenyl porphyrin (Zn-TCPP), wherein the antibody inhibits an enzymatic activity of gelatinase A as measured by ELISA, wherein the antibody has a dissociation constant for said Co-TCPP of no greater than $9 \times 10^{-8}$ M and wherein said antigen recognition region binds a pro-enzyme form of said gelatinase A with a lower affinity than an active form of said gelatinase A.

2. The isolated antibody of claim 1, wherein said antigen recognition region binds to said chelator in an absence of said zinc or cobalt ion with a lower affinity than to said metal ion bound chelator.

3. The isolated antibody of claim 1, capable of inhibiting 50% of an activity of said gelatinase A at a concentration less than $10^{-7}$ M.

4. A composition comprising the isolated antibody of claim 1 and a physiologically acceptable carrier.

5. The antibody of claim 1, generated by injecting into an animal a metal ion bound chelator at least three times.

6. An isolated antibody comprising an antigen recognition region which binds Cobalt(II)-tetra-carbozyl phenyl porphyrin (Co-TCPP) or Zinc (II)-tetra-carboxy phenyl porphyrin (Zn-TCPP), wherein the antibody inhibits an enzymatic activity of gelatinase A as measured by ELISA, wherein said antigen recognition region binds a pro-enzyme form of said gelatinase A with a lower affinity than an active form of said gelatinase A, and wherein antibody is generated by injecting into an animal an ion-bound chelator so as to obtain a serum titer of antibody of at least 1:20,000.

* * * * *